(12) United States Patent
Chang et al.

(10) Patent No.: US 11,937,964 B2
(45) Date of Patent: Mar. 26, 2024

(54) SYSTEMS AND METHODS FOR CONTROLLING AN X-RAY IMAGING DEVICE

(71) Applicant: SHANGHAI UNITED IMAGING HEALTHCARE CO., LTD., Shanghai (CN)

(72) Inventors: Yunheng Chang, Shanghai (CN); Tao Cai, Shanghai (CN); Yong E, Shanghai (CN); Qianqian Yu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 183 days.

(21) Appl. No.: 17/105,710

(22) Filed: Nov. 27, 2020

(65) Prior Publication Data

US 2021/0077050 A1    Mar. 18, 2021

Related U.S. Application Data

(63) Continuation of application No. PCT/CN2019/089646, filed on May 31, 2019.

(30) Foreign Application Priority Data

May 31, 2018  (CN) .......................... 201810548288.4
Aug. 23, 2018  (CN) .......................... 201810965672.4
Dec. 12, 2018  (CN) .......................... 201811518714.6

(51) Int. Cl.
*A61B 6/00*    (2006.01)
*A61B 6/04*    (2006.01)
*A61B 90/00*   (2016.01)

(52) U.S. Cl.
CPC .......... *A61B 6/5205* (2013.01); *A61B 6/4441* (2013.01); *A61B 6/466* (2013.01);
(Continued)

(58) Field of Classification Search
CPC ............ A61B 2090/366; A61B 6/0492; A61B 6/4405; A61B 6/4441; A61B 6/466;
(Continued)

(56) References Cited

U.S. PATENT DOCUMENTS 6,351,513 B1 * 2/2002 Bani-Hashemi ..... A61B 6/5247
378/19
2008/0198968 A1 * 8/2008 Takekoshi .............. A61B 6/462
378/62
(Continued)

FOREIGN PATENT DOCUMENTS

CN     2587369 Y    11/2003
CN     1806771 A     7/2006
(Continued)

OTHER PUBLICATIONS

Machine translation of CN-107393531 (Year: 2017).*
(Continued)

*Primary Examiner* — Dani Fox
*Assistant Examiner* — Soorena Kefayati
(74) *Attorney, Agent, or Firm* — METIS IP LLC

(57) ABSTRACT

The present disclosure provides systems and methods for controlling an X-ray imaging device. The method may include causing an X-ray source to emit X-rays to irradiate a subject. The method may also include generating an X-ray image of the subject. The X-ray image may be generated using a detector that is arranged to face the X-ray source to detect a portion of the X-rays that pass through the subject. And the method may further include causing to project, using an optical projection device, the X-ray image of the subject on a surface of the subject.

20 Claims, 15 Drawing Sheets

(52) U.S. Cl.
CPC .............. *A61B 6/54* (2013.01); *A61B 6/0492* (2013.01); *A61B 6/5258* (2013.01); *A61B 2090/366* (2016.02)

(58) Field of Classification Search
CPC ....... A61B 6/5205; A61B 6/5258; A61B 6/54; A61B 2560/4093; A61B 2560/0487; A61B 2090/064; G06F 3/011; G06F 3/017; G06F 3/0304; G06F 3/041; G06F 3/0481; G06F 3/0482; G06F 3/04847; G06F 3/0488; G06F 9/453; G16H 40/67; G16H 30/20; G16H 30/40
See application file for complete search history.

(56) References Cited

U.S. PATENT DOCUMENTS

| | | | | |
|---|---|---|---|---|
| 2008/0232554 | A1* | 9/2008 | Heigl | A61B 6/4441 378/197 |
| 2009/0082784 | A1* | 3/2009 | Meissner | A61B 34/30 606/130 |
| 2009/0103678 | A1* | 4/2009 | Abe | A61B 6/08 378/98.3 |
| 2009/0271035 | A1* | 10/2009 | Lurz | B25J 9/1664 700/245 |
| 2010/0020926 | A1* | 1/2010 | Boese | A61B 6/5241 359/9 |
| 2011/0270123 | A1* | 11/2011 | Reiner | A61B 6/469 600/558 |
| 2012/0201352 | A1* | 8/2012 | Dennerlein | G01N 23/046 378/62 |
| 2013/0218340 | A1* | 8/2013 | Hager | B25J 9/1671 700/257 |
| 2013/0342350 | A1* | 12/2013 | Popescu | G08B 21/02 340/573.1 |
| 2014/0267255 | A1* | 9/2014 | Graumann | A61B 6/487 345/419 |
| 2014/0286477 | A1* | 9/2014 | Ishii | A61B 6/4291 378/62 |
| 2015/0003674 | A1* | 1/2015 | Eun | A61B 6/08 382/103 |
| 2015/0230768 | A1* | 8/2015 | Belei | A61B 6/4405 378/62 |
| 2015/0253979 | A1* | 9/2015 | Popescu | G06F 3/011 715/771 |
| 2015/0281680 | A1* | 10/2015 | Grafenberg | H04N 13/167 348/50 |
| 2016/0135767 | A1* | 5/2016 | Kim | A61B 6/08 378/62 |
| 2016/0166333 | A1* | 6/2016 | Wang | A61B 34/10 600/476 |
| 2016/0367169 | A1* | 12/2016 | Hardie | A61B 5/743 |
| 2017/0042631 | A1* | 2/2017 | Doo | H04N 13/398 |
| 2017/0119329 | A1* | 5/2017 | Warner | A61B 90/36 |
| 2017/0209110 | A1* | 7/2017 | Kiraly | A61B 6/44 |
| 2017/0238897 | A1* | 8/2017 | Siewerdsen | A61B 6/466 |
| 2017/0303874 | A1* | 10/2017 | Lee | H04N 5/222 |
| 2018/0121041 | A1* | 5/2018 | Schweizer | G06F 3/041 |
| 2018/0130202 | A1* | 5/2018 | Wang | A61B 6/5217 |
| 2018/0168736 | A1* | 6/2018 | Yang | A61B 5/061 |
| 2018/0260997 | A1* | 9/2018 | Petkov | G06F 18/214 |
| 2018/0325618 | A1* | 11/2018 | Justin | A61B 90/37 |
| 2019/0005646 | A1* | 1/2019 | Grass | G06T 7/337 |
| 2019/0059914 | A1* | 2/2019 | Nguyen | A61B 6/4482 |
| 2019/0192100 | A1* | 6/2019 | Fischer | A61B 6/5235 |
| 2019/0192105 | A1* | 6/2019 | Mewes | A61B 6/583 |

FOREIGN PATENT DOCUMENTS

| | | | |
|---|---|---|---|
| CN | 1839754 | A | 10/2006 |
| CN | 1937959 | A | 3/2007 |
| CN | 104586505 | A | 5/2015 |
| CN | 104665852 | A | 6/2015 |
| CN | 104799874 | A | 7/2015 |
| CN | 106333747 | A | 1/2017 |
| CN | 107174753 | A | 9/2017 |
| CN | 107393531 | A | 11/2017 |
| CN | 107393531 | A * | 11/2017 |
| CN | 107978315 | A | 5/2018 |
| CN | 108039171 | A | 5/2018 |
| CN | 108175510 | A | 6/2018 |
| CN | 108392271 | A | 8/2018 |
| CN | 109102873 | A | 12/2018 |
| CN | 109157235 | A | 1/2019 |
| CN | 109620274 | A | 4/2019 |
| JP | H08336518 | A | 12/1996 |
| JP | 2006334096 | A | 12/2006 |
| JP | 2017051410 | A | 3/2017 |

OTHER PUBLICATIONS

The Extended European Search Report in European Application No. 19810160.2 dated May 28, 2021, 6 pages.
International Search Report in PCT/CN2019/089646 dated Aug. 30, 2019, 5 pages.
Written Opinion in PCT/CN2019/089646 dated Aug. 30, 2019, 6 pages.
First Office Action in Chinese Application No. 201810965672.4 dated Jul. 31, 2020, 18 pages.
First Office Action in Chinese Application No. 201811518714.6 dated Dec. 16, 2019, 17 pages.
First Office Action in Chinese Application No. 201810548288.4 dated Apr. 22, 2020, 16 pages.

* cited by examiner

900

910 — Determining a first coordinate indicating a position of a load in a first coordinate system related to maneuvering of a mechanical arm supporting the load 920 — Obtaining a three dimensional (3D) image of the subject, the 3D image representing the subject in a second coordinate system 930 — Determining a relationship between the first coordinate system and the second coordinate system 940 — Transforming the first coordinate in the first coordinate system to a second coordinate in the second coordinate system 950 — Displaying a representation of the load in the 3D image at the second coordinate in the second coordinate system

Determining one or more mechanical parameters associated with the mechanical arm — 1120

Determining the first coordinate indicating the position of the load in the first coordinate system based on the one or more mechanical parameters — 1140

| Acquiring a first parameter associated with a rotation of the at least one joint or a second parameter associated with a translation of the at least one joint | 1220 |

↓

| Determining the position information of the at least one joint of the mechanical arm based on the first parameter associated with the rotation of the at least one joint or the second parameter associated with the translation of the at least one joint | 1240 |

FIG. 12

SYSTEMS AND METHODS FOR CONTROLLING AN X-RAY IMAGING DEVICE

CROSS-REFERENCE TO RELATED APPLICATIONS

This application is a continuation of International Application No. PCT/CN2019/089646 filed on May 31, 2019, which claims priority of Chinese Patent Application No. 201810965672.4 filed on Aug. 23, 2018, Chinese Patent Application No. 201811518714.6 filed on Dec. 12, 2018, and Chinese Patent Application No. 201810548288.4 filed on May 31, 2018, the entire contents of each of which are hereby incorporated by reference.

TECHNICAL FIELD

The present disclosure generally relates to imaging device operation, and more particularly, relates to systems and methods for controlling an X-ray imaging device.

BACKGROUND

An X-ray imaging device is a medical imaging equipment commonly used in diagnosis and treatment. In order to view internal organs (e.g., the organs under the skin tissue) of a patient, the X-ray imaging device may be caused to radiate the patient with X-rays to generate an image of the internal organs. An operator may adjust the position of the X-ray imaging device according to the image displayed on a screen. By simply watching the image, which shows the positions of the internal organs in an image coordinate system, the operator cannot quickly and accurately locate the organs in the coordinate system where the patient locates (e.g., the world coordinate system). As a result, the operator may need to adjust the X-ray imaging device multiple times and gradually locate the positions of the organs, which extends the operation time and increase the dose of X-rays exposed to the patient. Therefore, it is desirable to provide systems and methods for controlling the X-ray imaging device in a more efficient way.

SUMMARY

In some aspects of the present disclosure, a method is provided. The method may be implemented on a computing device having one or more processors and one or more storage media. The method may include causing an X-ray source to emit X-rays to irradiate a subject. The method may further include generating an X-ray image of the subject. The X-ray image may be generated using a detector that is arranged to face the X-ray source to detect a portion of the X-rays that pass through the subject. And the method may further include causing to project, using an optical projection device, the X-ray image of the subject on a surface of the subject.

In some embodiments, the causing to project, using an optical projection device, the X-ray image of the subject on a surface of the subject may include causing to project at least part of the X-ray image on the surface of the subject at a region where the X-rays irradiate the subject.

In some embodiments, the X-ray source and the detector may be installed at two ends of a C-arm of an X-ray imaging device, respectively.

In some embodiments, the method may further include causing to adjust, using an adjustment device, a position of at least one of the X-ray source or the detector relative to the subject based on the projected X-ray image.

In some embodiments, the method may further include causing to generate, using an optical positioning device, a position mark within the projected X-ray image on the surface of the subject.

In some embodiments, the optical positioning device may be a laser positioning device coupled to the C-arm.

In some embodiments, the optical projection device may include a driver board, a display panel, and a light source. The causing to project, using the optical projection device, the X-ray image of the subject on the surface of the subject may include causing, using the driver board, the display panel to display the X-ray image, and causing to emit, using the light source, a light towards the display panel to project the displayed X-ray image on the surface of the subject.

In some embodiments, the optical projection device may include a lens arranged between the display panel and the subject, and a distance between the display panel and the lens is adjustable.

In some embodiments, the method may further include causing to receive, by a workstation, the X-ray image of the subject, and transmitting the X-ray image to the optical projection device.

In some embodiments, the method may further include navigating a mechanical arm, the mechanical arm supporting a load and being mechanically connected to the C-arm. The method may include determining a first coordinate indicating a position of the load in a first coordinate system related to maneuvering of the mechanical arm. The method may further include obtaining a three dimensional (3D) image of the subject, the 3D image representing the subject in a second coordinate system. The method may further include determining a relationship between the first coordinate system and the second coordinate system. The method may further include transforming the first coordinate in the first coordinate system to a second coordinate in the second coordinate system. And the method may further include displaying a representation of the load in the 3D image at the second coordinate in the second coordinate system.

In some embodiments, the first coordinate system and the second coordinate system may be associated with different coordinate origins. The determining a relationship between the first coordinate system and the second coordinate system may include calculating a mapping relationship between the first coordinate system and the second coordinate system.

In some embodiments, the obtaining a 3D image of the subject may include obtaining a plurality of two dimensional (2D) images based on scan data acquired by the detector at different positions, and reconstructing the 3D image based on the plurality of 2D images.

In some embodiments, the reconstructing the 3D image based on the plurality of 2D images may include correcting the plurality of 2D images, and reconstructing the 3D image based on the plurality of corrected 2D images.

In some embodiments, the determining a first coordinate indicating a position of the load in a first coordinate system may include determining one or more mechanical parameters associated with the mechanical arm, and determining the first coordinate indicating the position of the load in the first coordinate system based on the one or more mechanical parameters.

In some embodiments, the determining one or more mechanical parameters associated with the mechanical arm may include determining position information of at least one joint of the mechanical arm or type information of the load.

In some embodiments, the determining position information of at least one joint of the mechanical arm may include acquiring a first parameter associated with a rotation of the at least one joint or a second parameter associated with a translation of the at least one joint, and determining the position information of the at least one joint of the mechanical arm based on the first parameter associated with the rotation of the at least one joint or the second parameter associated with the translation of the at least one joint.

In some embodiments, the acquiring a first parameter associated with a rotation of the at least one joint or a second parameter associated with a translation of the at least one joint may include acquiring the first parameter associated with the rotation of the at least one joint or the second parameter associated with the translation of the at least one joint by at least one sensor periodically.

In some embodiments, the type information of the load may include at least one of an electric drill, a living sampling device, a catheter, or a laser light.

In some embodiments, the method may further include obtaining a plurality of sets of training data, each set of the training data including an indication signal that is derived from an operator and represents an order to operate the C-arm and an operation signal that is directed to operate the C-arm in response to the indication signal. The method may further include establishing a relationship between the indication signals and the operation signals. The method may further include acquiring at least one test indication signal. The method may further include determining, based on the relationship, at least one candidate operation signal in response to the at least one test indication signal. The method may further include determining whether the at least one candidate operation signal is accurately responding to the at least one test indication signal. And the method may further include in response to a determination that the at least one candidate operation signal is not accurately responding to the at least one test indication signal, updating the relationship based on the at least one test indication signal.

In some embodiments, the relationship between the indication signals and the operation signals may be represented by a relational database or a specific model.

In some embodiments, the at least one test indication signal may include a plurality of test indication signals. And the determining whether the at least one candidate operation signal is accurately responding to the at least one test indication signal may include determining a matching rate between the plurality of test indication signals and the corresponding candidate operation signals.

In some embodiments, the determination that the at least one candidate operation signal is not accurately responding to the at least one test indication signal may include that the matching rate between the plurality of test indication signals and the corresponding candidate operation signals is lower than a preset value.

In some embodiments, the indication signals may include at least one of a voice command or an image command, and the operation signals include at least one of a position adjustment, a parameter setting, or a starting of X-ray imaging with the X-ray imaging device.

In some embodiments, the image command may include image data of the operator's gesture action.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 9 is a flowchart illustrating an exemplary process for navigating a mechanical arm according to some embodiments of the present disclosure;

FIG. 11 is a flowchart illustrating an exemplary process for determining a first coordinate indicating a position of a load in a first coordinate system according to some embodiments of the present disclosure;

FIG. 12 is a flowchart illustrating an exemplary process for determining position information of at least one joint of the mechanical arm according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
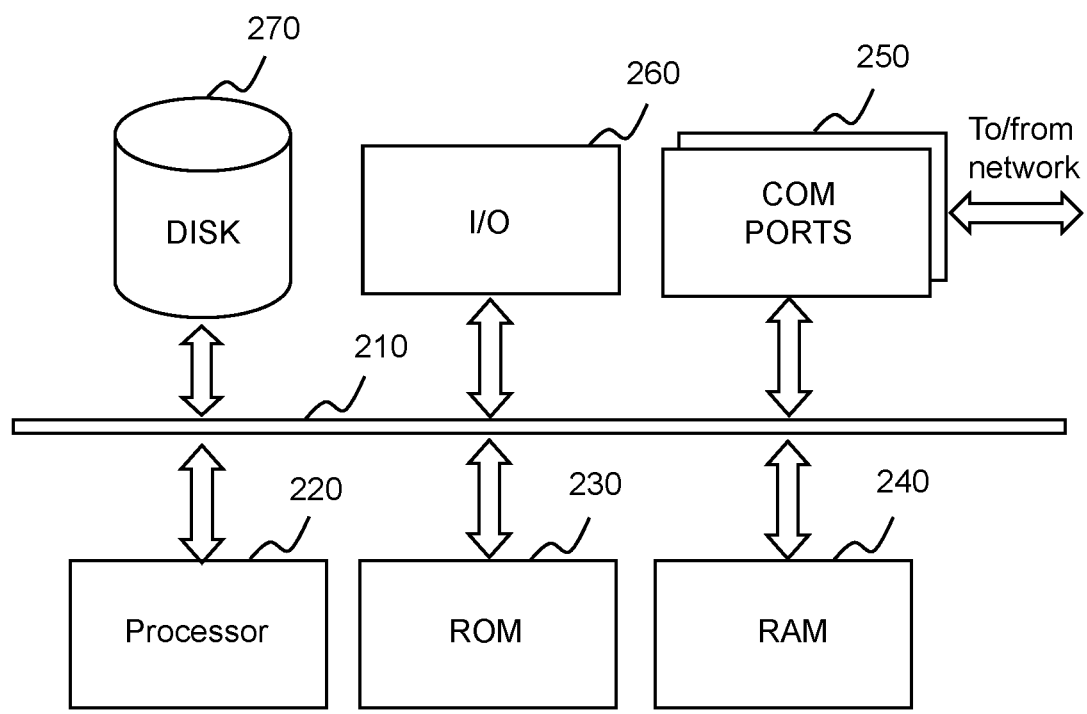
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., the processor 220 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The following description is provided to help better understanding the processing methods and/or systems. This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

Provided herein are systems and methods for controlling an X-ray imaging device, such as for disease diagnosis, disease treatment, or research purposes. The systems may perform the methods to emit, from an X-ray source, X-rays to irradiate a subject, and detect, by a detector that is arranged to face the X-ray source, a portion of the X-rays that pass through the subject to generate an X-ray image of the subject. The systems may further perform the methods to project, by an optical projection device, the X-ray image of the subject on a surface of the subject at a region where the X-rays irradiate the subject. By doing so, the systems and methods provided herein may provide a spatial mapping relationship between the subject and the X-ray image thereof, thus helping an operator to better locate an internal organ of the subject based on the projected image displayed on the surface of the subject.

In another aspect of the present disclosure, systems and methods for navigating a mechanical arm supporting a load and being mechanically connected to a C-arm are provided. The systems may perform the methods to determine a first coordinate indicating a position of the load in a first coordinate system related to maneuvering of the mechanical arm. The systems may perform the methods to obtain a three dimensional (3D) image of the subject, the 3D image representing the subject in a second coordinate system. The systems may perform the methods to determine a relationship between the first coordinate system and the second coordinate system. The systems may also perform the methods to transform the first coordinate in the first coordinate system to a second coordinate in the second coordinate system. And the systems may further perform the methods to display a representation of the load in the 3D image at the second coordinate in the second coordinate system. The systems and methods provided herein may precisely show the spatial relationship between the load and the subject in the 3D image, thus facilitating the subsequent operation of the load within the subject.

In still another aspect of the present disclosure, systems and methods for training an X-ray imaging device are provided. The systems may perform the methods to establish a relationship between the indication signals and the operation signals. The systems may perform the methods to acquire at least one test indication signal. The systems may perform the methods to determine, based on the relationship, at least one candidate operation signal in response to the at least one test indication signal. The systems may perform the methods to determine whether the at least one candidate operation signal is accurately responding to the at least one test indication signal. And in response to a determination that the at least one candidate operation signal is not accurately responding to the at least one test indication signal, the systems may perform the methods to update the relationship based on the at least one test indication signal. The systems and methods provided herein may simplify the operation of using the X-ray imaging device by an operator (e.g., a doctor, a technician), thereby facilitating the diagnosis and treatment of the subject.

Figure 1:
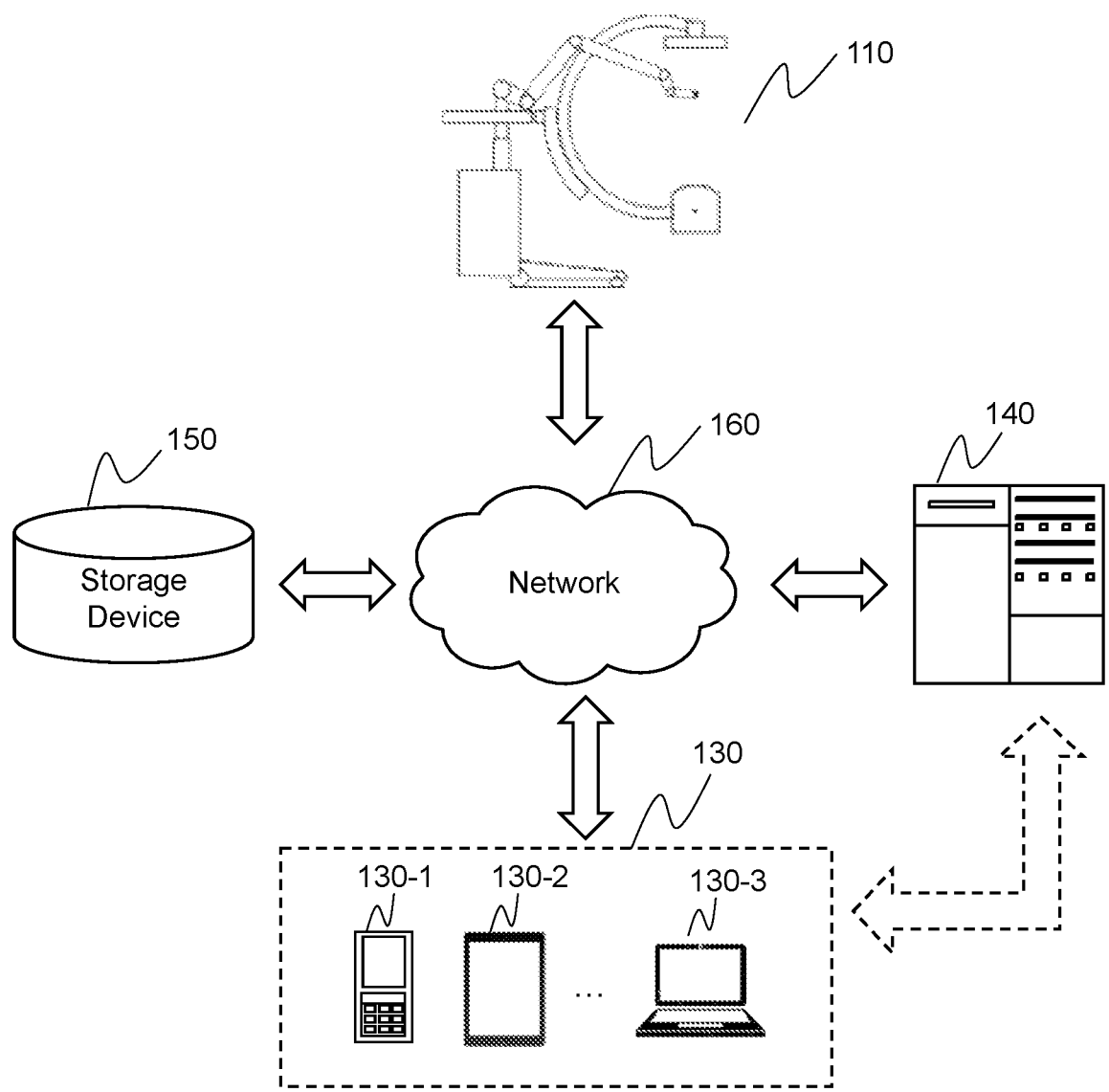
FIG. 1 is a schematic diagram illustrating an exemplary X-ray imaging system according to some embodiments of the present disclosure.

FIG. 1 is a schematic diagram illustrating an exemplary X-ray imaging system according to some embodiments of the present disclosure. The X-ray imaging system 100 may be configured to perform a diagnosis and/or a treatment on a subject (not shown). For example, the diagnosis may be performed on human organs such as bones, hearts, livers, or the like. The treatment may be a surgical operation such as a puncture, a biopsy, an ablation (e.g., a radiofrequency ablation), a grinding (e.g., a bone grinding), a drilling (e.g., a bone drilling), an implantation (e.g., a radioactive seed implantation), a suction, or the like. The subject may include a patient, a portion of the patient (e.g., an organ and/or a tissue of the patient), a man-made object (e.g., a phantom), etc.

As shown in FIG. 1, the X-ray imaging system 100 may include an X-ray imaging device 110, one or more terminals 130, a processing device 140, a storage device 150, a network 160. The connection between the components in the X-ray imaging system 100 may be variable. Merely by way of example, as illustrated in FIG. 1, the X-ray imaging device 110 may be connected to the processing device 140 through the network 160. As another example, the X-ray imaging device 110 may be connected to the processing device 140 directly. As a further example, the storage device 150 may be connected to the processing device 140 directly or through the network 160. As still a further example, the terminal 130 may be connected to the processing device 140 directly (as indicated by the bi-directional arrow in dotted lines linking the terminal 130 and the processing device 140) or through the network 160.

The X-ray imaging device 110 may be configured to perform a scan on the subject to generate scan data before, during, and/or after a diagnosis and/or a treatment. In some embodiments, one or more X-ray images of the subject may be reconstructed based on the scan data by the processing device 140. In some embodiments, the one or more X-ray images of the subject may be projected on a surface of the subject by the processing device 140 for a diagnosis and/or a treatment. For example, the X-ray imaging device 110 may perform a scan on the subject before the surgical operation and an X-ray image of the subject may be generated based on the scan data. The X-ray image may indicate a lesion of the subject and be used as a basis for planning a surgical route of a surgical equipment. As another example, the X-ray imaging device 110 may scan the subject during the treatment in real-time or periodically to monitor the position of the surgical equipment.

The X-ray imaging device 110 may include a computed tomography (CT) device (e.g., a cone beam CT), a digital radiography (DR) device, or the like. In some embodiments, the X-ray imaging device 110 may be a multi-modality imaging device including, for example, a PET-CT device, or the like.

In some embodiments, the X-ray imaging device 110 may include a C-arm machine and an optical projection device. The C-arm machine may include an X-ray source to emit X-rays and a detector to detect the X-rays that pass through the subject. The optical projection device may be communicatively connected to the C-arm machine and project the X-ray image received from the processing device 140 on a specific target (e.g., a surface of the subject). More descriptions regarding the C-arm machine may be found elsewhere in the present disclosure (e.g., FIGS. 7, 13 and the description thereof). More descriptions regarding the optical projection device may be found elsewhere in the present disclosure (e.g., FIG. 8 and the description thereof).

In some embodiments, the X-ray imaging device 110 may also include a workstation (not shown), to which the processing device 140 may transmit the X-ray image. The optical projection device may be communicatively connected to the workstation to receive the X-ray image from the workstation.

In some embodiments, the X-ray imaging system 100 may correspond to one or more coordinate systems. For example, the motion of the X-ray imaging device 110 (or a part of the X-ray imaging device 110) may be represented in a first coordinate system (e.g., the world coordinate system), and the X-ray image reconstructed from the scan data of the X-ray imaging device 110 may represent the subject in a second coordinate system (e.g., the image coordinate system) different from the first coordinate system. The coordinate system(s) may have any number of dimensions and the dimensions may be in any directions. Merely by way of example, the coordinate system(s) may include a Cartesian coordinate system and/or a world coordinate system including three dimensions. The coordinate origin(s) of the coordinate system(s) may be located at any suitable position. For example, the coordinate origin of the Cartesian coordinate system may be located at the iso-center of the X-ray imaging device 110.

The terminal 130 may be configured to realize an interaction between a user and one or more components of the X-ray imaging system 100. For example, the terminal 130 may have a user interface (UI) for the user to input an instruction to the X-ray imaging device 110 to perform a scan on the subject. As another example, the terminal 130 may display one or more images acquired by the X-ray imaging system 100 to the user. The terminal 130 may include a mobile device 130-1, a tablet computer 130-2, a laptop computer 130-3, a display 130-4, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal 130 may be part of the processing device 140.

The processing device 140 may process data and/or information related to the X-ray imaging system 100, for example, information obtained from the X-ray imaging device 110, the terminal 130, and/or the storage device 150. For example, the processing device 140 may receive scan data of the subject from the X-ray imaging device 110 and reconstruct an X-ray image of the subject based on the scan data. As another example, the processing device 140 may reconstruct the X-ray image of the subject and send the reconstructed image to the optical projection device to project on a surface of the subject. As still another example, the processing device 140 may send the reconstructed image of the subject to a workstation of the X-ray imaging device 110, and the workstation of the X-ray imaging device 110 may further send the reconstructed image to the optical projection device to project on the surface of the subject. In some embodiments, the processing device 140 may be a single server or a server group. The server group may be centralized or distributed. In some embodiments, the processing device 140 may be local to or remote from other components of the X-ray imaging system 100. For example, the processing device 140 may access information and/or data stored in the X-ray imaging device 110, the terminal 130, and/or the storage device 150 via the network 160. As another example, the processing device 140 may be directly connected to the X-ray imaging device 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2. In some embodiments, the processing device 140 may be integrated into the X-ray imaging device 110 to form part of the X-ray imaging device 110.

The storage device 150 may store data, instructions, and/or any other information. In some embodiments, the storage device 150 may store data obtained from the X-ray imaging device 110, the terminal 130, and the processing device 140. In some embodiments, the storage device 150 may store data and/or instructions that the processing device 140 and/or the terminal 130 may execute or use to perform exemplary methods described in the present disclosure. In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 160 to communicate with one or more other components in the X-ray imaging system 100 (e.g., the processing device 140, the terminal 130, etc.). One or more components in the X-ray imaging system 100 may access the data or instructions stored in the storage device 150 via the network 160. In some embodiments, the storage device 150 may be directly connected to or communicate with one or more other components in the X-ray imaging system 100 (e.g., the X-ray imaging device 110, the processing device 140, the terminal 130, etc.). In some embodiments, the storage device 150 may be part of the processing device 140.

The network 160 may include any suitable network that can facilitate exchange of information and/or data in the X-ray imaging system 100. In some embodiments, one or more components of the X-ray imaging system 100 (e.g., the X-ray imaging device 110, the terminal 130, the processing device 140, and/or the storage device 150) may communicate with each other via the network 160. For example, the processing device 140 may obtain scan data from the storage device 150 via the network 160. As another example, the X-ray imaging device 110 may obtain user instructions from the terminal 130 via the network 160. The network 160 may include a public network (e.g., the Internet), a private network (e.g., a local area network (LAN), a wide area network (WAN), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 160 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 160 may include one or more network access points. For example, the network 160 may include wired and/or wireless network access points such as base stations and/or internet exchange points through which one or more components of the X-ray imaging system 100 may be connected to the network 160 to exchange data and/or information.

It should be noted that the above description of the X-ray imaging system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the X-ray imaging system 100 may include one or more additional components. Additionally or alternatively, one or more components of the X-ray imaging system 100 described above may be omitted. For example, the X-ray imaging system 100 may further include an imaging device other than the X-ray imaging device 110, which is configured to capture an image of the subject during the diagnosis and/or the treatment.

FIG. 2 is a schematic diagram illustrating exemplary hardware and/or software components of an exemplary computing device according to some embodiments of the present disclosure. In some embodiments, one or more components of the X-ray imaging system 100 may be implemented on one or more components of the computing device 200. Merely by way of example, the processing device 140 and/or the terminal 130 may be implemented on one or more components of the computing device 200, respectively.

As illustrated in FIG. 2, the computing device 200 may include a communication bus 210, a processor 220, a storage, an input/output (I/O) 260, and a communication port 250. The processor 220 may execute computer instructions (e.g., program code) and perform functions of one or more components of the X-ray imaging system 100 (e.g., the processing device 140) in accordance with techniques described herein. The computer instructions may include, for example, routines, programs, objects, components, data structures, procedures, modules, and functions, which perform particular functions described herein. In some embodiments, the processor 220 may include interface circuits and processing circuits therein. The interface circuits may be configured to receive electronic signals from the communication bus 210, wherein the electronic signals encode structured data and/or instructions for the processing circuits to process. The processing circuits may conduct logic calculations, and then determine a conclusion, a result, and/or an instruction encoded as electronic signals. Then the interface circuits may send out the electronic signals from the processing circuits via the communication bus 210.

Merely for illustration, only one processor 220 is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage may store data/information related to the X-ray imaging system 100, such as information obtained from the X-ray imaging device 110, the terminal 130, the storage device 150, and/or any other component of the X-ray imaging system 100. In some embodiments, the storage may include a mass storage, a removable storage, a volatile read-and-write memory, a random access memory (RAM) 240, a read-only memory (ROM) 230, a disk 270, or the like, or any combination thereof. In some embodiments, the storage may store one or more programs and/or instructions to perform exemplary methods described in the present disclosure. For example, the storage may store a program for the processing device 140 for controlling the X-ray imaging device 110.

The I/O 260 may input and/or output signals, data, information, etc. In some embodiments, the I/O 260 may enable a user interaction with the computing device 200. In some embodiments, the I/O 260 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 250 may be connected to a network (e.g., the network 160) to facilitate data communications. The communication port 250 may establish connections between the computing device 200 (e.g., the processing device 140) and the X-ray imaging device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 250 may be and/or include a standardized communication port, such as RS232, RS485, etc. In some embodiments, the communication port 250 may be a specially designed communication port. For example, the communication port 250 may be designed in accordance with the digital imaging and communications in medicine (DICOM) protocol.

Figure 3:
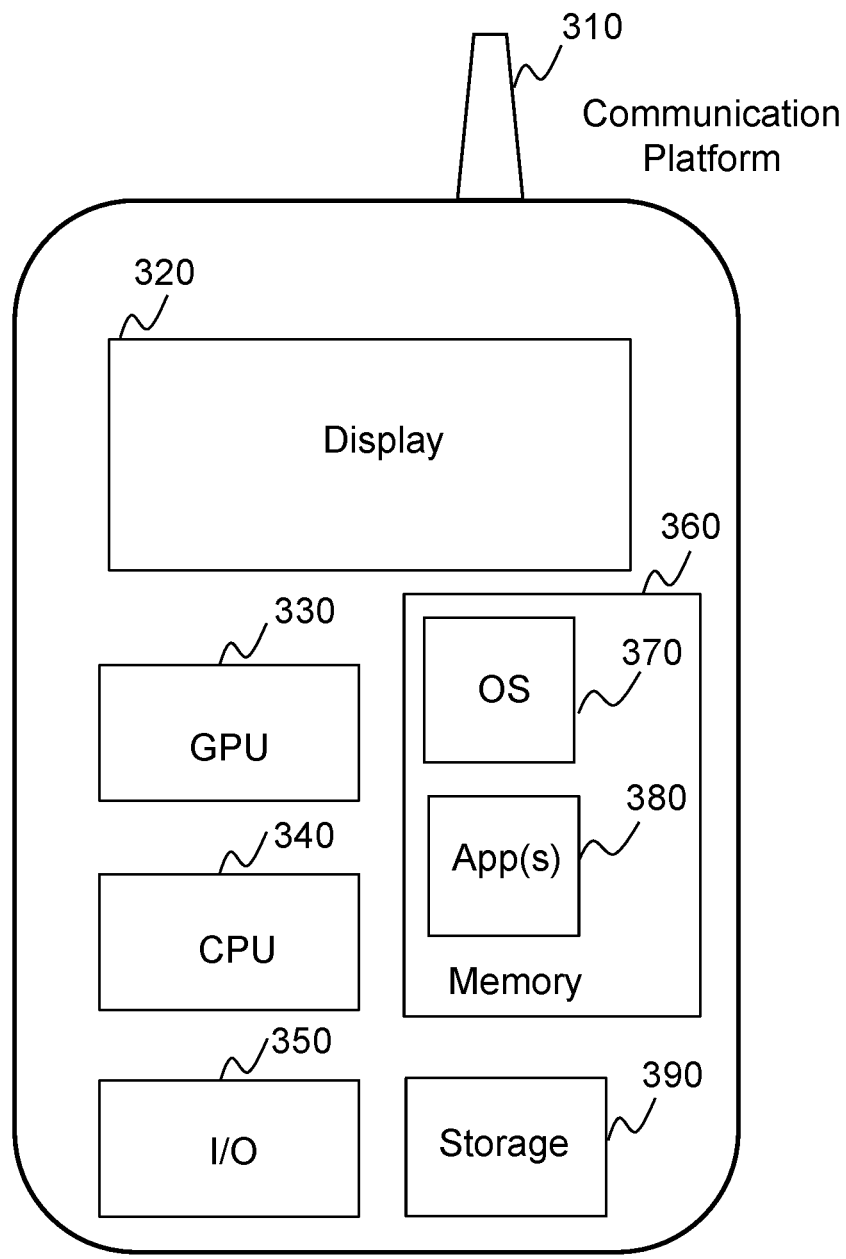
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, one or more components of the X-ray imaging system 100 may be implemented on one or more components of the mobile device 300. Merely by way of example, the terminal 130 may be implemented on one or more components of the mobile device 300.

As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™' Windows Phone™, etc.) and one or more applications 380 may be loaded into the memory 360 from the storage 390 in order to be executed by the CPU 340. The applications 380 may include a browser or any other suitable mobile apps for receiving and rendering information relating to the X-ray imaging system 100. User interactions with the information stream may be achieved via the I/O 350 and provided to one or more components of the X-ray imaging system 100 via the network 160.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
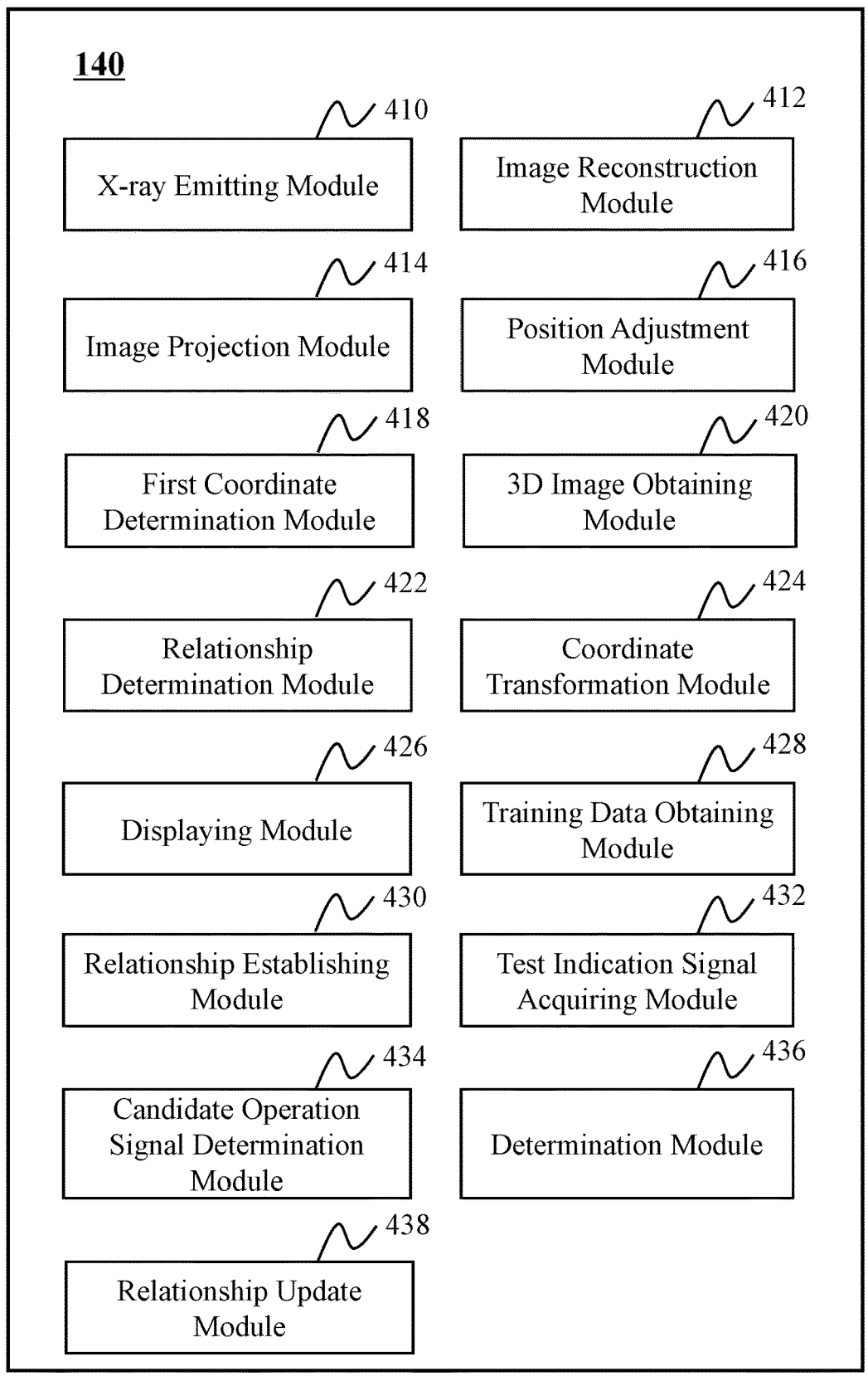
FIG. 4 is a block diagram illustrating an exemplary processing device according to some embodiments of the present disclosure.

FIG. 4 is a block diagram illustrating an exemplary processing device according to some embodiments of the present disclosure. The processing device 140 may include an X-ray emitting module 410, an image reconstruction module 412, an image projection module 414, a position adjustment module 416, a first coordinate determination module 418, a 3D image obtaining module 420, a relationship determination module 422, a coordinate transformation module 424, a displaying module 426, a training data obtaining module 428, a relationship establishing module 430, a test indication signal acquiring module 432, a candidate operation signal determination module 434, a determination module 436, and a relationship update module 438. One or more of the modules of the processing device 140 may be interconnected. The connection(s) may be wireless or wired.

Figure 7:
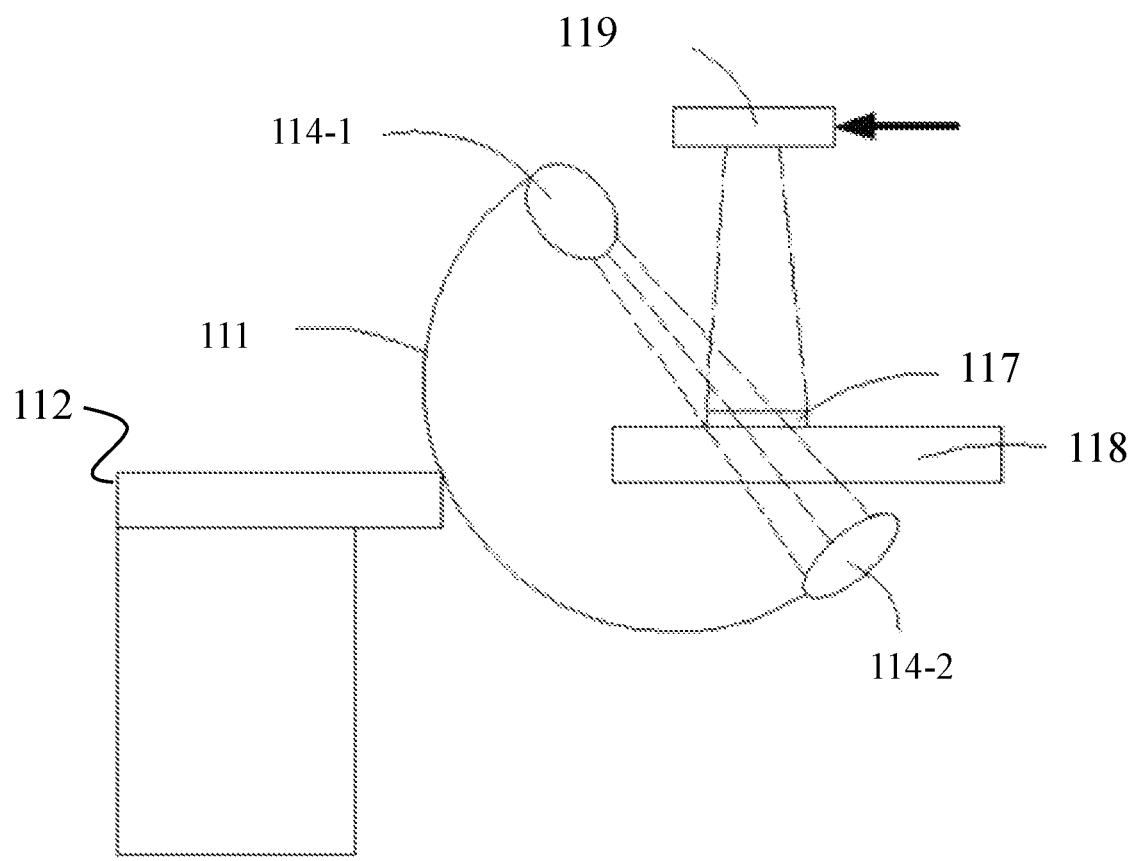
FIG. 7 is a schematic diagram illustrating an exemplary X-ray imaging device according to some embodiments of the present disclosure.
Figure 13:
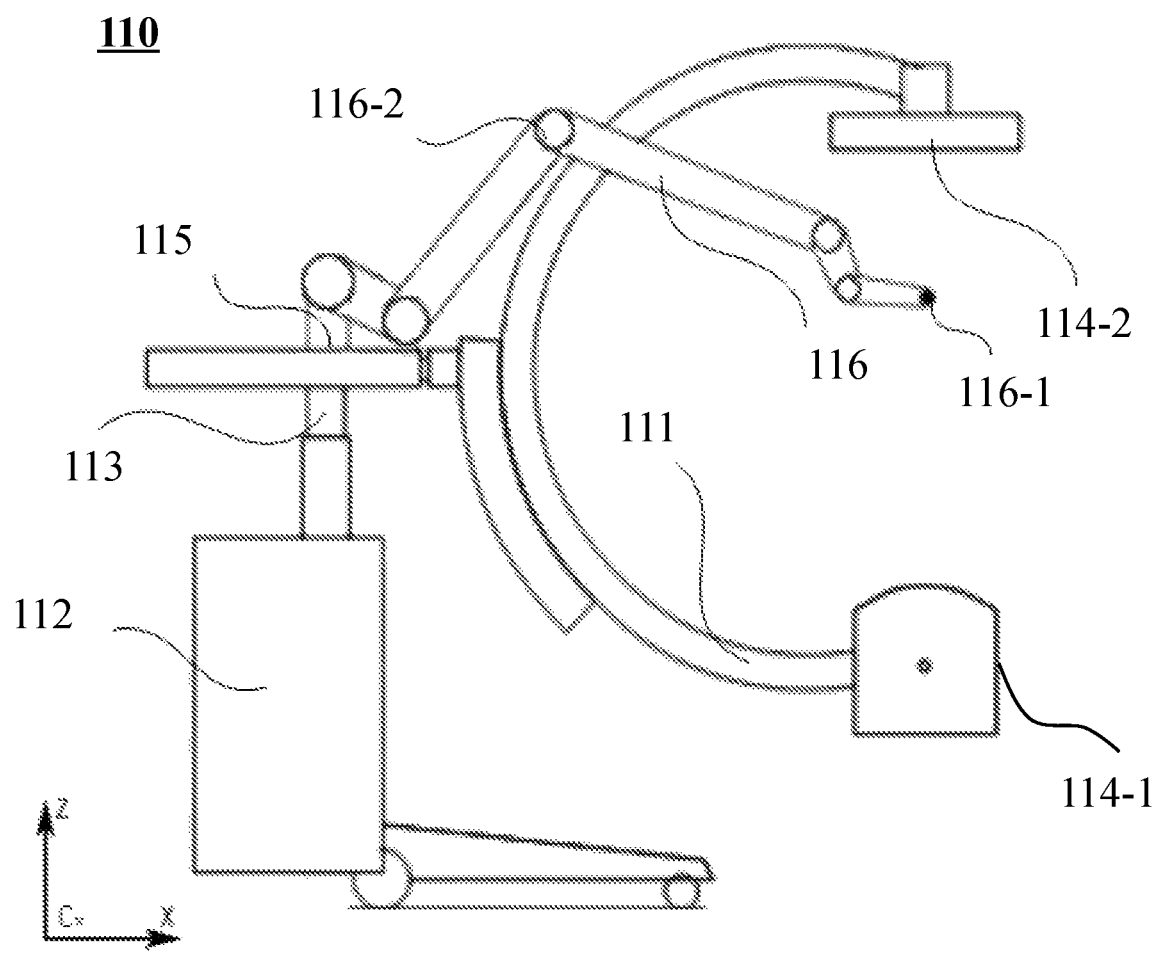
FIG. 13 is a schematic diagram illustrating an exemplary X-ray imaging device according to some embodiments of the present disclosure.

The X-ray emitting module 410 may be configured to cause an X-ray source to emit X-rays to irradiate a subject. In some embodiments, the subject may be a patient, a portion of the patient (e.g., an organ and/or a tissue of the patient), a man-made object (e.g., a phantom), or the like, or any combination thereof. Optionally, the subject may be placed on a table (not shown in figures of the present disclosure) of the X-ray imaging device 110. In some embodiments, The X-ray source may be a component of the X-ray imaging device 110. For example, the X-ray source may be installed at one end of a C-arm of the X-ray imaging device 110 (e.g., the X-ray source 114-1 as shown in FIG. 7 and FIG. 13). In some embodiments, the X-rays may be generated by the X-ray source according to a certain principle (e.g., a Bremsstrahlung principle).

The image reconstruction module 412 may be configured to generate an X-ray image of the subject. In some embodiments, the X-ray image may be generated using scan data of a detector. The detector may be arranged to face the X-ray source to detect the X-rays that pass through the subject. In some embodiments, the X-ray source and the detector are installed at two ends of a C-arm of an X-ray imaging device, respectively. For example, the X-ray source may be installed at one end of a C-arm of the X-ray imaging device 110 (e.g., the X-ray source 114-1 as shown in FIG. 7 and FIG. 13), and the detector may be installed at another end of the C-arm of the X-ray imaging device 110 (e.g., the detector 114-2 as shown in FIG. 7 and FIG. 13) to face the X-ray source. In some embodiment, the X-ray image of the subject may be generated from the scan data according to a reconstruction algorithm. In some embodiment, the X-ray image of the subject may be stored in a storage (e.g., the storage device 150), displayed on a screen of a user terminal (e.g., the terminal 130), or sent to a workstation connected to the X-ray imaging device 110 for further processing.

The image projection module 414 may be configured to cause to project, using an optical projection device, the X-ray image of the subject on a surface of the subject. In some embodiments, the X-ray imaging system 100 may include a workstation (not shown). The image projection module 414 may be configured to send the X-ray image of the subject to the workstation, and cause to receive, by the workstation, the X-ray image of the subject. In some embodiments, the image projection module 414 may be configured to directly transmit the X-ray image to the optical projection device for projection. The image projection module 414 may transmit the X-ray image to the optical projection device in real time or at regular intervals.

In some embodiments, the image projection module 414 may be configured to cause the optical projection device to project at least part of the X-ray image on the surface of the subject at a region where the X-rays irradiate the subject.

In some embodiments, the image projection module 414 may be configured to cause to generate, using an optical positioning device, a position mark within the projected X-ray image on the surface of the subject. In some embodiments, the optical positioning device may be a laser positioning device. The laser positioning device may produce laser beams to shoot on the surface of the subject and form the position mark. The position mark may be easily recognized by an operator (e.g., a doctor, a technician).

The position adjustment module 416 may be configured to cause to adjust, using an adjustment device, a position of at least one of the X-ray source or the detector relative to the subject based on the projected X-ray image. In some embodiments, the position adjustment module 416 may be configured to cause to adjust, using an adjustment device, the position of the X-ray source and/or the detector relative to the subject to a new position according to the instructions of an operator (e.g., a doctor, a technician).

The first coordinate determination module 418 may be configured to determine a first coordinate indicating a position of a load in a first coordinate system related to maneuvering of the mechanical arm supporting the load.

In some embodiments, the first coordinate determination module 418 may be configured to establish a first coordinate system related to the maneuvering of the mechanical arm. And the movement information of the mechanical arm may be represented by the first coordinate system. Since the load of the mechanical arm is fixed on the mechanical arm, the first coordinate indicating the position of the load in the first coordinate system may be determined after the first coordinate system is determined.

In some embodiments, the first coordinate determination module 418 may be configured to determine one or more mechanical parameters associated with the mechanical arm, and then determine the first coordinate indicating the position of the load in the first coordinate system based on the one or more mechanical parameters. To determine the one or more mechanical parameters associated with the mechanical arm, the first coordinate determination module 418 may be configured to determine the position information of at least one joint of the mechanical arm or type information of the load. Specifically, the first coordinate determination module 418 may be configured to acquire a first parameter associated with a rotation of the at least one joint or a second parameter associated with the translation of the at least one joint by at least one sensor periodically, and then determine the position information of the at least one joint of the mechanical arm based on the first parameter associated with the rotation of the at least one joint or the second parameter associated with the translation of the at least one joint. In some embodiments, the type information of the load may comprise at least one of an electric drill, a living sampling device, a catheter, or a laser light as described above.

The 3D image obtaining module 420 may be configured to obtain a three dimensional (3D) image of the subject. The 3D image may represent the subject in a second coordinate system. In some embodiments, the 3D image obtaining module 420 may be configured to obtain a plurality of two dimensional (2D) images based on scan data acquired by the detector at different positions. Optionally, the 3D image obtaining module 420 may be configured to correct the plurality of 2D images. And the 3D image obtaining module 420 may be configured to reconstruct the 3D image based on the plurality of (corrected) 2D images to obtain a three dimensional (3D) image of the subject.

The relationship determination module 422 may be configured to determine a relationship between the first coordinate system and the second coordinate system.

In some embodiments, the first coordinate system and the second coordinate system may have different coordinate origins. In some embodiments, the relationship may be a mapping relationship. The mapping relationship may refer to a relationship between first coordinates of one or more points in the first coordinate system and their corresponding second coordinates in the second coordinate system. In some embodiments, the mapping relationship between the first coordinate system and the second coordinate system may be in any form such as a table, a matrix, a function, or the like, or any combination thereof.

The coordinate transformation module 424 may be configured to transform the first coordinate in the first coordinate system to a second coordinate in the second coordinate system. In some embodiments, the coordinate transformation module 424 may be configured to transform the first coordinate in the first coordinate system to the second coordinate in the second coordinate system based on the relationship between the first coordinate system and the second coordinate system.

The displaying module 426 may be configured to display a representation of the load in the 3D image at the second coordinate in the second coordinate system. In some embodiments, the representation of the load may be a mark in any form. For example, the mark of the load may be, for example, a figure or pattern that is distinctive from the voxels in the 3D image. Exemplary marks may include a pre-stored 3D model that resembles the actual shape of the load, a point with a specific color, or the like.

The training data obtaining module 428 may be configured to obtain a plurality of sets of training data. Each set of the training data may include an indication signal and an operation signal.

In some embodiments, the indication signal may be derived from an operator (e.g., a doctor, a technician) and represent an order to operate the X-ray imaging device 110. The indication signal may include at least one of a voice command or an image command.

In some embodiments, the indication signal may be collected by an acquisition device such as a visible light sensor (e.g., a camera), and/or an audio sensor (e.g., a microphone). The acquisition device may be installed on the X-ray imaging device 110 or other device near the X-ray imaging device 110 to monitor a region where the operator appears.

The relationship establishing module 430 may be configured to establish a relationship between the indication signals and the operation signals. In some embodiments, the relationship between the indication signals and the operation signals may be represented by a relational database or a specific model.

In some embodiments, the relationship establishing module 430 may be configured to establish the relationship between the indication signals and the operation signals based on a plurality of sets of indication signals and operation signals using a machine learning process including a neural network.

In some embodiments, the relationship establishing module 430 may be configured to establish the relationship between the indication signals and the operation signals using a specific model. Specifically, the relationship establishing module 430 may collect and/or record indication signals of a first operator and corresponding operation signals of a second operator, for example, in a preset time period. And the relationship establishing module 430 may train the specific model using the collected and/or recorded signals. In the training process, the indication signals may be used as inputs of the specific model and the operation signals may be used as the corresponding outputs. After specific model is trained with sufficient training data, the relationship establishing module 430 may obtain an operation signal as the output of the trained model when using an indication signal as the input of the trained model.

The test indication signal acquiring module 432 may be configured to acquire at least one test indication signal to test whether the relationship between the indication signals and the operation signals is accurate.

In some embodiments, the test indication signal acquiring module 432 may be configured to acquire the at least one test indication signal from an operator (e.g. a doctor). In some embodiments, the test indication signal acquiring module 432 may be configured to acquire the at least one test indication signal using a simulated technique.

The candidate operation signal determination module 434 may be configured to determine, based on the relationship, at least one candidate operation signal in response to the at least one test indication signal.

In some embodiments, the candidate operation signal determination module 434 may be configured to determine the at least one candidate operation signal in response to the at least one test indication signal based on the relational database. In some embodiments, the candidate operation signal determination module 434 may be configured to determine the at least one candidate operation signal in response to the at least one test indication signal based on the trained model.

The determination module 436 may be configured to determine whether the at least one candidate operation signal is accurately responding to the at least one test indication signal.

In some embodiments, a second operator may evaluate whether the at least one candidate operation signal is accurately responding to the at least one test indication signal through the determination module 436.

In some embodiments, the at least one test indication signal may include a plurality of test indication signals, and the determination module 436 may be configured to determine whether the at least one candidate operation signal is accurately responding to the at least one test indication signal by determining a matching rate between the plurality of test indication signals and the corresponding candidate operation signals. The matching rate may indicate an accuracy of the processing device 140 for predicting candidate operation signals according to the test indication signals and the established relationship between the indication signals and the operation signals. Specifically, the determination module 436 may be configured to determine a matching rate between the plurality of test indication signals and the corresponding candidate operation signals, and determine whether the matching rate between the plurality of test indication signals and the corresponding candidate operation signals satisfies a condition. In some embodiments, the determination module 43 may determine a preset value for the matching rate, and the condition may be that the matching rate is lower than the preset value. If the matching rate is lower than the preset value, the determination module 436 may determine that the corresponding candidate operation signals are not accurately responding to the plurality of test indication signals. And if the matching rate is not lower than the preset value, the determination module 436 may determine that the corresponding candidate operation signals are accurately responding to the plurality of test indication signals.

The relationship update module 438 may be configured to, in response to a determination that the at least one candidate operation signal is not accurately responding to the at least one test indication signal, update the relationship based on the at least one test indication signal.

In some embodiments, the relationship update module 438 may be configured to update the relational database to include the at least one test indication signal and its corresponding operation signal(s). In some embodiments, the relationship update module 438 may be configured to update the relational database to modify existing relations between the indication signals and an operation signals if there is an error or conflict. In some embodiments, if a missing corresponding relation is found, for example, a specific indication signal (e.g., the indication signal of a specific operator) has no corresponding operation signal, or the indication signals of a specific operator have not been recorded, the relationship update module 438 may be configured to add the missing corresponding relation into the relational database.

It should be noted that the above description of the processing device 140 is merely provided for the purpose of illustration, and not intended to limit the scope of the present disclosure. For persons having ordinary skills in the art, various variations and modifications may be performed in the light of the present disclosure. However, those variations and modifications do not depart from the scope of the present disclosure. For example, one or more of the modules of the processing device 140 mentioned above may be omitted or integrated into a single module. As another example, the processing device 140 may include one or more additional modules, for example, a storage module for data storage.

Figure 5:
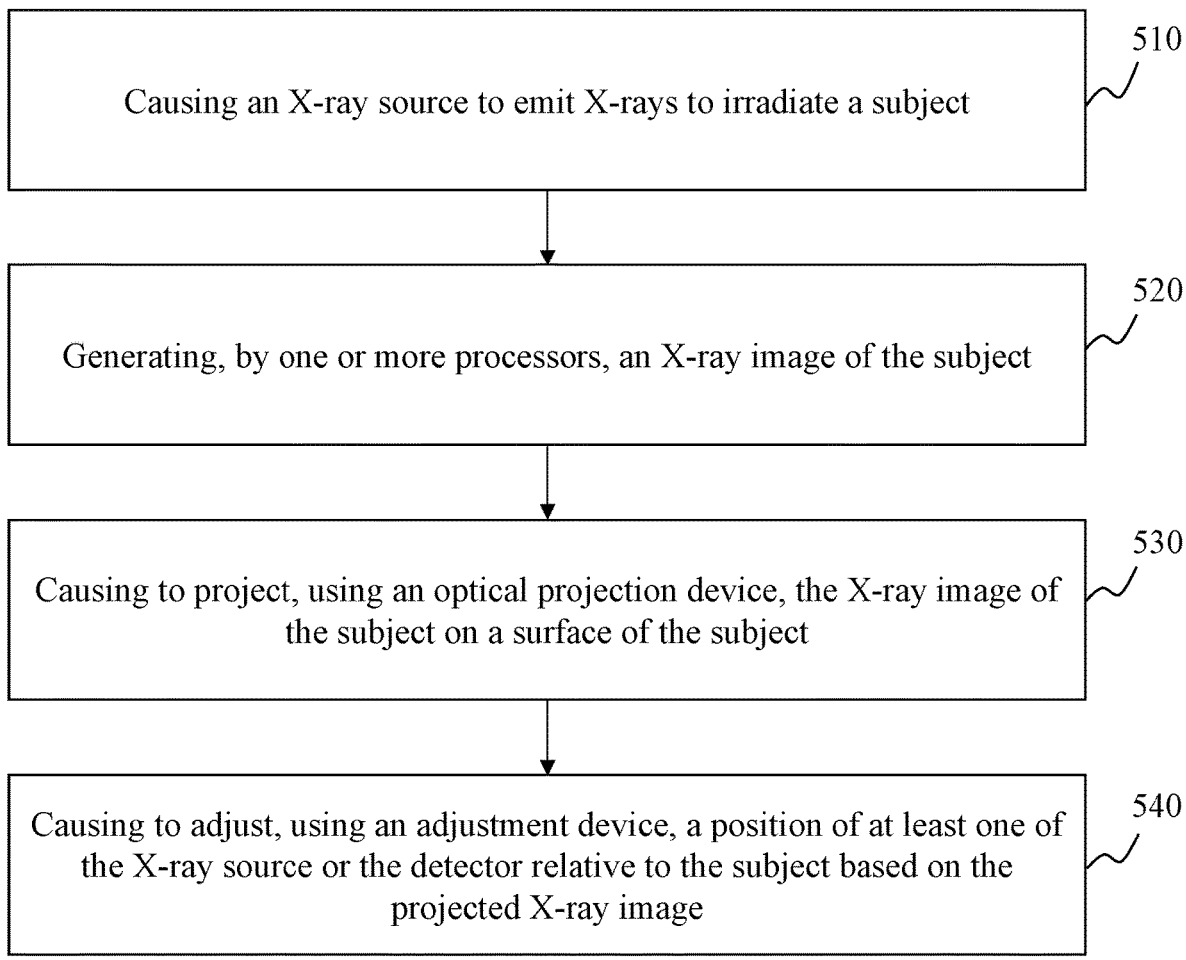
FIG. 5 is a flowchart illustrating an exemplary process for controlling an X-ray imaging device according to some embodiments of the present disclosure.

FIG. 5 is a flowchart illustrating an exemplary process 500 for controlling an X-ray imaging device according to some embodiments of the present disclosure. In some embodiments, the process 500 may be executed by the X-ray imaging system 100. For example, the process 500 may be implemented as a set of instructions (e.g., an application) stored in one or more storage devices (e.g., the storage device 150, the ROM 230, and/or RAM 240) and invoked and/or executed by the processing device 140 (implemented on, for example, the processor 220 of the computing device 200, the CPU 340 of the mobile device 300, and/or the modules illustrated in FIG. 4). The operations of the process 500 presented below are intended to be illustrative. In some embodiments, the process may be accomplished with one or more additional operations not described, and/or without one or more of the operations discussed. Additionally, the order of the operations of the process 500 as illustrated in FIG. 5 and described below is not intended to be limiting.

In 510, the processing device 140 (e.g., the X-ray emitting module 410) may cause an X-ray source to emit X-rays to irradiate a subject.

The subject may be a patient, a portion of the patient (e.g., an organ and/or a tissue of the patient), a man-made object (e.g., a phantom), or the like, or any combination thereof. Optionally, the subject may be placed on a table (not shown in figures of the present disclosure) of the X-ray imaging device 110.

The X-ray source may be a component of the X-ray imaging device 110. For example, the X-ray source may be installed at one end of a C-arm of the X-ray imaging device 110 (e.g., an X-ray source 114-1 as shown in FIG. 7 and FIG. 13). The X-rays may be generated by the X-ray source according to a certain principle (e.g., a Bremsstrahlung principle). Specifically, the X-ray source may include an X-ray tube which may generate X-rays with a power supply provided by a high voltage generator. The X-ray tube may at least include an anode and a cathode. The cathode may include one or more filaments (e.g., a tungsten wire, an iridium wire, a nickel wire, a molybdenum wire) configured to emit free electrons under a radiation voltage. The free electrons may be accelerated in an electric field between the cathode and the anode to form an electron beam striking the anode to further generate X-rays. The anode may be located opposite to the cathode and may be made of an electrically conductive material, and may have a high mechanical strength under a high temperature and have a high melting point. Exemplary materials may include titanium zirconium molybdenum (TZM), ferrum, cuprum, tungsten, graphite, or the like, or an alloy thereof, or any combination thereof. The subject may be irradiated by the X-rays generated by the X-ray source. And a portion of the X-rays may pass through or be scattered by the subject.

In 520, the processing device 140 (e.g., the image reconstruction module 412) may generate an X-ray image of the subject.

In some embodiments, the X-ray image may be generated using scan data of a detector. The detector may be arranged to face the X-ray source to detect the X-rays that pass through the subject. For example, the X-ray source may be installed at one end of a C-arm of the X-ray imaging device 110 (e.g., the X-ray source 114-1 as shown in FIG. 7 and FIG. 13), and the detector may be installed at another end of the C-arm of the X-ray imaging device 110 (e.g., the detector 114-2 as shown in FIG. 7 and FIG. 13) to face the X-ray source.

In some embodiment, the X-ray image of the subject may be generated from the scan data according to a reconstruction algorithm such as, an iterative reconstruction algorithm (e.g., a statistical reconstruction algorithm), a Fourier slice theorem algorithm, a fan-beam reconstruction algorithm, an analytic reconstruction algorithm, an algebraic reconstruction technique (ART), a simultaneous algebra reconstruction technique (SART), a filtered back projection (FBP) technique, a Feldkamp-Davis-Kress (FDK) reconstruction technique, or the like, or any combination thereof. In some embodiment, the X-ray image of the subject may be stored in a storage (e.g., the storage device 150), displayed on a screen of a user terminal (e.g., the terminal 130), or sent to a workstation connected to the X-ray imaging device 110 for further processing.

In 530, the processing device 140 (e.g., the image projection module 414) may cause to project, using an optical projection device, the X-ray image of the subject on a surface of the subject.

In some embodiments, the X-ray imaging system 100 may include a workstation (not shown). The processing device 140 (e.g., the image projection module 414) may send the X-ray image of the subject to the workstation. For example, the X-ray image of the subject may be transmitted to an image processor installed on the workstation for further processing, such as, using the optical projection device for projecting the X-ray image of the subject.

In some embodiments, the processing device 140 (e.g., the image projection module 414) may directly transmit the X-ray image to the optical projection device for projection. The processing device 140 (e.g., the image projection module 414) may transmit the X-ray image to the optical projection device in real time or at regular intervals.

In some embodiments, the optical projection device may include one or more optical components. More descriptions regarding the optical projection device may be found elsewhere in the present disclosure (e.g., FIG. 8 and the description thereof).

In some embodiments, the processing device 140 (e.g., the image projection module 414) may cause the optical projection device to project at least part of the X-ray image on the surface of the subject at a region where the X-rays irradiate the subject. For example, in the case that the region where the X-rays irradiate the subject is the region including the liver of the subject (i.e., the X-rays traverses the liver of the subject), the X-ray image may at least include the liver of the patient. Then, the processing device 140 may cause the optical projection device to project the X-ray image on the surface of the subject at the region including the liver of the subject. Specifically, the liver represented in the projected X-ray image may have the same or similar size as the real liver of the subject. By doing so, the liver represented in the projected X-ray image may be used to reflect the information (e.g., the position, the structure) of the real liver in the subject. Details regarding the projection of the X-ray image may be found elsewhere in the present disclosure (e.g., FIG. 6 and the relevant descriptions thereof).

In 540, the processing device 140 (e.g., the position adjustment module 416) may cause to adjust, using an adjustment device, a position of at least one of the X-ray source or the detector relative to the subject based on the projected X-ray image.

In some embodiments, the adjustment device may adjust the position of the X-ray source and/or the detector relative to the subject to a new position according to the instructions of an operator (e.g., a doctor, a technician). For example, the operator may determine whether the projected X-ray image is accurately displaying the region of interest he/she wants. If the region represented in the projected X-ray image deviates from the region of interest, the operator may operate the adjustment device to adjust the position of the X-ray source and/or the detector. At the new position, the X-ray source and the detector may generate another X-ray image to be projected by the optical projection device on the surface of the subject.

In some embodiments, the X-ray imaging device may have a C-arm similar to the C-arm 111 illustrated in FIG. 7, on which the X-ray source and the detector are installed. The adjustment device may be a mechanical device (e.g., an electric motor) connected to the C-arm, and may adjust the position of the X-ray source and/or the detector relative to the subject by rotating the C-arm.

In some embodiments, the adjustment of the position of the X-ray source and/or the detector may be realized by a manual operation of the operator. For example, the operator may input parameters regarding the adjustment of the position of the X-ray source and/or the detector, or manually drag the C-arm to a new position. In some embodiments, the adjustment of the position of the X-ray source and/or the detector may be automatic. For example, the X-ray imaging device 110 may include a learning module which can be trained with historical projected X-ray images and corresponding subsequent manual operations of the operator (or one or more adjustment parameters associated with the corresponding subsequent manual operations). After training, the learning module may be able to calculate one or more adjustment parameters, such as the direction and/or angle of the rotation of the C-arm based on a received projected X-ray image. Then the adjustment parameters may be sent to a control module of the X-ray imaging device to automatically adjust the position of at least one of the X-ray source and/or the detector accordingly.

In some embodiments, the processing device 140 (e.g., the image projection module 414) may cause to generate, using an optical positioning device, a position mark within the projected X-ray image on the surface of the subject. In some embodiments, the optical positioning device may be a laser positioning device. The laser positioning device may produce laser beams to shoot on the surface of the subject and form the position mark. The position mark may be easily recognized by an operator (e.g., a doctor, a technician).

In some embodiments, the laser positioning device may be coupled to the C-arm of the X-ray imaging device 110. For example, the laser positioning device may be coupled to the C-arm 111 illustrated in FIG. 7. More specifically, the laser positioning device may be coupled to a position of the C-arm that is near the X-ray source to ensure that the laser beams emitted from the coupled position may be intersected with a region of the projected X-ray image on the surface of the subject. Further, the laser positioning device may move along with the C-arm, and the position mark generated by the laser positioning device may be located in the projected X-ray image on the surface of the subject to positioning the irradiating position of the X-ray source. In some embodiments, the position mark may have any suitable shape, such as the shape of a cross. The center of the cross may be used as an anchor point for determining the irradiating position of the X-ray source. Accordingly, an operator may adjust the C-arm according to the position mark to improve the accuracy of the irradiating position of the X-ray source.

Those skilled in the art may understand that the optical positioning device is not limited to producing a laser beam. And the shape of the position mark is not limited to a cross. Any other shape (e.g., a point, a star, a triangle, a circle, etc.) that may achieve a similar positioning function may also be used according to some embodiments of the present disclosure. In some embodiments, if the position mark is a point, the point may be used as the anchor point for determining the irradiating position of the X-ray source. If the position mark is a cross as described above, the center of the cross may be used as the anchor point anchor point for determining the irradiating position of the X-ray source.

Specifically, when the operator uses the X-ray imaging device to project an X-ray image of the subject, the position mark generated by the optical positioning device may be shot on the surface of the subject to reflect the irradiating position of the X-ray source of the X-ray imaging device. The operator may analyze the X-ray image projected on the surface of the subject, and determine a desired irradiating position of the X-ray source accordingly. Then, the operator may only need to adjust the position of the C-arm to move the position mark to a target position associated with the desired irradiating position of the X-ray source, and then take shoots using the X-ray source to obtain the desired image.

In some embodiments, the optical positioning device may be positioned between the X-ray source and the detector. A placement region of the subject may be formed between the optical positioning device and the detector. The placement region of the subject may be used to place the subject. That is to say, the optical positioning device may be located at a side of the subject opposite to the detector.

It should be understood that the optical positioning device (e.g., the laser positioning device) may be a standalone device. For example, the optical positioning device may be independently coupled to a gantry adjacent to the X-ray imaging device 110.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may include one or more additional operations or one or more of the operations mentioned above may be omitted. For example, the operation 540 may be omitted. In some embodiments, an operation of the process 500 may be divided into a plurality of sub-operations.

Figure 6:
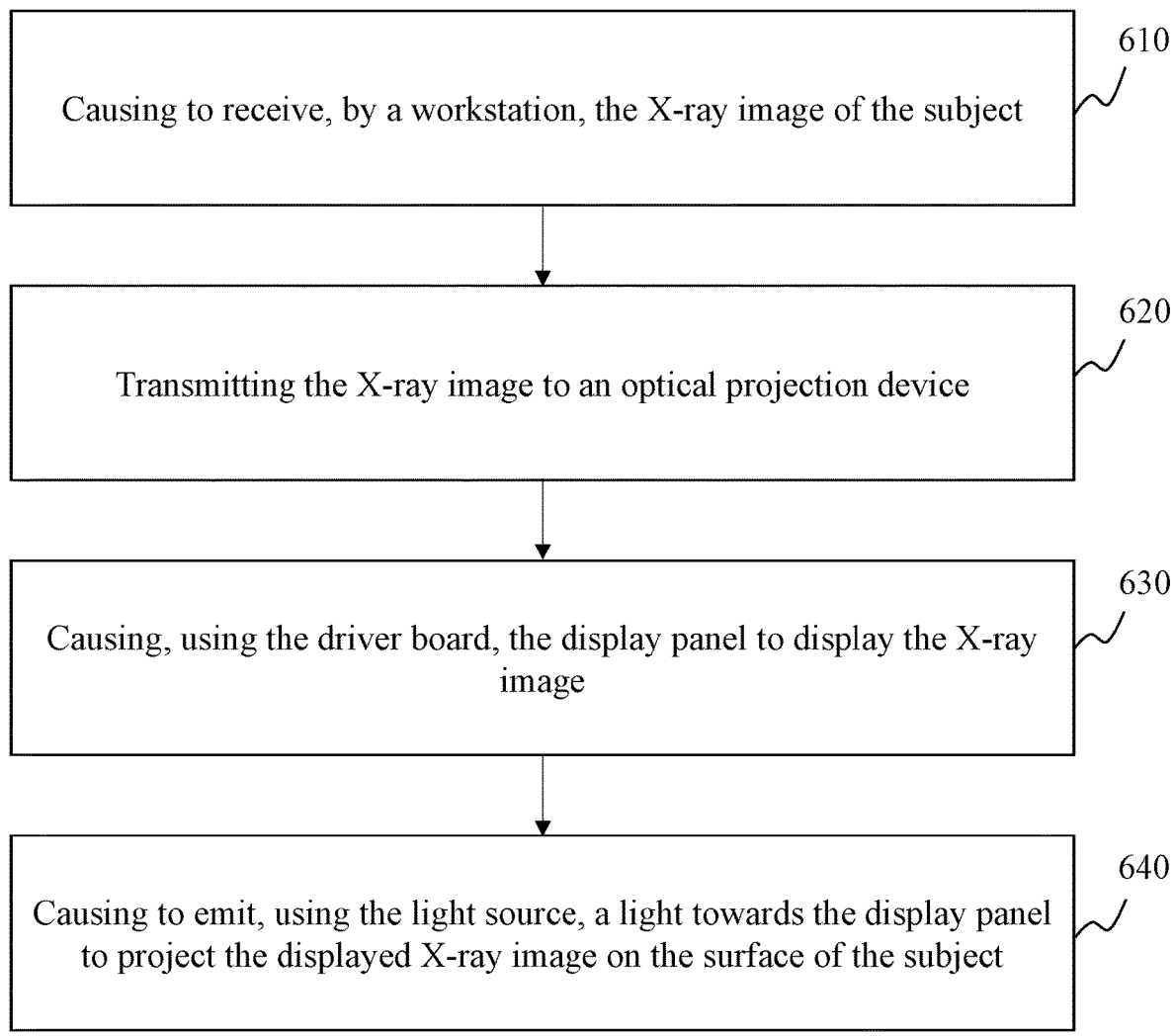
FIG. 6 is a flowchart illustrating an exemplary process for projecting an X-ray image according to some embodiments of the present disclosure.

FIG. 6 is a flowchart illustrating an exemplary process for projecting an X-ray image according to some embodiments of the present disclosure. In some embodiments, the process 600 may be executed by the X-ray imaging system 100. For example, the process 600 may be implemented as a set of instructions (e.g., an application) stored in one or more storage devices (e.g., the storage device 150, the ROM 230, and/or RAM 240) and invoked and/or executed by the processing device 140 (implemented on, for example, the processor 220 of the computing device 200, the CPU 340 of the mobile device 300, and/or the modules illustrated in FIG. 4). The operations of the process 600 presented below are intended to be illustrative. In some embodiments, the process may be accomplished with one or more additional operations not described, and/or without one or more of the operations discussed. Additionally, the order of the operations of the process 600 as illustrated in FIG. 6 and described below is not intended to be limiting. In some embodiments, one or more operations of the process 600 may be performed to achieve operation 530.

In 610, the processing device 140 (e.g., the image projection module 414) may cause to receive, by a workstation, the X-ray image of the subject.

In some embodiments, the workstation may be embodied as a personal computer (PC) that is positioned near the X-ray imaging system 100 and hard-wired to the X-ray imaging system 100 via a communication link. The workstation may also be embodied as a portable computer such as a laptop computer or a hand-held computer that transmits information to, and receives information from, the X-ray imaging system 100. Optionally, the communication link may be a wireless communication link that enables information to be transmitted to or from the workstation wirelessly. In some embodiments, the workstation may be configured to control the operation of the X-ray imaging system 100 in real-time. The workstation may also be programmed to perform further processing of the X-ray image.

In some embodiments, the workstation may include a central processing unit (CPU) or a computer, a display, an input device, or the like. As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are not intended to limit in any way the definition and/or meaning of the term "computer". In some embodiments, the computer executes a set of instructions that are stored in one or more storage elements or memories, in order to process the X-ray image generated using the detector. The storage elements may also store data or other information as desired or needed. And the storage element may be in the form of an information source or a physical memory element located within the computer.

In some embodiments, the X-ray image generated by the detector may be transmitted to an image processor installed on the workstation for further processing (e.g., denoising).

In 620, the workstation may transmit the X-ray image to an optical projection device. The workstation may transmit the X-ray image to the optical projection device in real time or at regular intervals. The optical projection device may include a driver board, a display panel and a light source. In some embodiments, the driver board may be communicatively connected to the workstation. After receiving the X-ray image from the workstation, the driver board may drive the display panel to display the X-ray image. In some embodiments, the display panel 119-2 may be a liquid crystal panel without backlight. More descriptions regarding the structure of the optical projection device may be found elsewhere in the present disclosure (e.g., FIG. 8 and the description thereof).

In 630, the processing device 140 (e.g., the image projection module 414) may cause, using the driver board, the display panel to display the X-ray image.

In some embodiments, the X-ray image displayed on the display panel may be a grayscale image. In some embodiments, the optical projection device may further include a lens to zoom in or out the projected X-ray image on the surface of the subject. The lens may be arranged between the display panel and the subject. The distance between the optical projection device and the lens may be adjustable to achieve the zooming function.

In 640, the processing device 140 (e.g., the image projection module 414) may cause to emit, using the light source, a light towards the display panel to project the displayed X-ray image on the surface of the subject.

In some embodiments, the light source may project the X-ray image displayed on the display panel through the lens to the surface of the subject.

In some embodiments, the light source may be an LED (Light Emitting Diode) lamp, which may have a long service life and a uniform brightness, thereby ensuring projection effects of the optical projection device and prolonging service life of the optical projection device.

It should be understood that the aforementioned optical projection device including the driver board, the display panel, the light source and the lens is merely provided for illustration purpose. Those skilled in the art may think of many other combinations to be used to project the X-ray image on the surface of the subject.

In some embodiments, the processing device 140 (e.g., the image projection module 414) may cause to project at least part of the X-ray image on the surface of the subject at a region where the X-rays irradiate the subject. The at least part of the X-ray image may be projected on the surface of the subject so that the projected X-ray image may coincide with a position of the irradiate organs or tissues in the subject, which may help the operator to better locate a real position of the organs or tissues in the subject.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may include one or more additional operations or one or more of the operations mentioned above may be omitted. For example, the operation 610 may be omitted, and the X-ray image of the subject may be transmitted to the optical projection device directly from the processing device 140. As another example, the process 600 may include one or more additional operations to project the X-ray image of the subject on the surface of the subject. In some embodiments, an operation of the process 600 may be divided into a plurality of sub-operations.

FIG. 7 is a schematic diagram illustrating an exemplary X-ray imaging device according to some embodiments of the present disclosure. In some embodiments, the X-ray imaging device 110 may be configured to generate an X-ray image 117 of a subject 118, and project, using an optical projection device 119, the X-ray image 117 of the subject 118 on the surface of the subject 118.

As shown in FIG. 7, the X-ray imaging device 110 may be a C-arm machine. The C-arm machine may include a C-arm 111, an X-ray source 114-1, a detector 114-2, and a gantry 112, or the like. The C-arm 111 may be installed on the gantry 112, and the X-ray source 114-1 may emit X-rays (as shown in dotted lines in FIG. 7) towards the detector 114-2. The X-ray source 114-1 and the detector 114-2 may be installed at two ends of the C-arm 111 of the X-ray imaging device 110, respectively. The gantry 112 may be stationary (i.e., not movable relative to the ground), or may be movable relative to the ground.

In some embodiments, the X-ray imaging device 110 may include or be communicatively connected to a workstation (not shown), to which the X-ray image 117 may be transmitted. The optical projection device 119 may be communicatively connected to the workstation to receive the X-ray image 117 for projection.

In some embodiments, the X-ray imaging device 110 may also include an adjustment device (not shown) configured to adjust a position of at least one of the X-ray source 114-1 or the detector 114-2 relative to the subject 118 based on the projected X-ray image 117. Alternatively, the adjustment device may be configured to rotate the C-arm 111 to adjust the position of the X-ray source 114-1 or the detector 114-2.

In some embodiments, the X-ray imaging device 110 may include an optical positioning device (not shown) which may be used to generate a position mark within the projected X-ray image 117 on the surface of the subject 118. The optical positioning device may be a laser positioning device coupled to the C-arm 111.

It should be noted that the above description of the X-ray imaging device 110 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the X-ray imaging device 110 may include one or more additional components. In some embodiments, one or more components of the X-ray imaging device 110 described above may be omitted.

Figure 8:
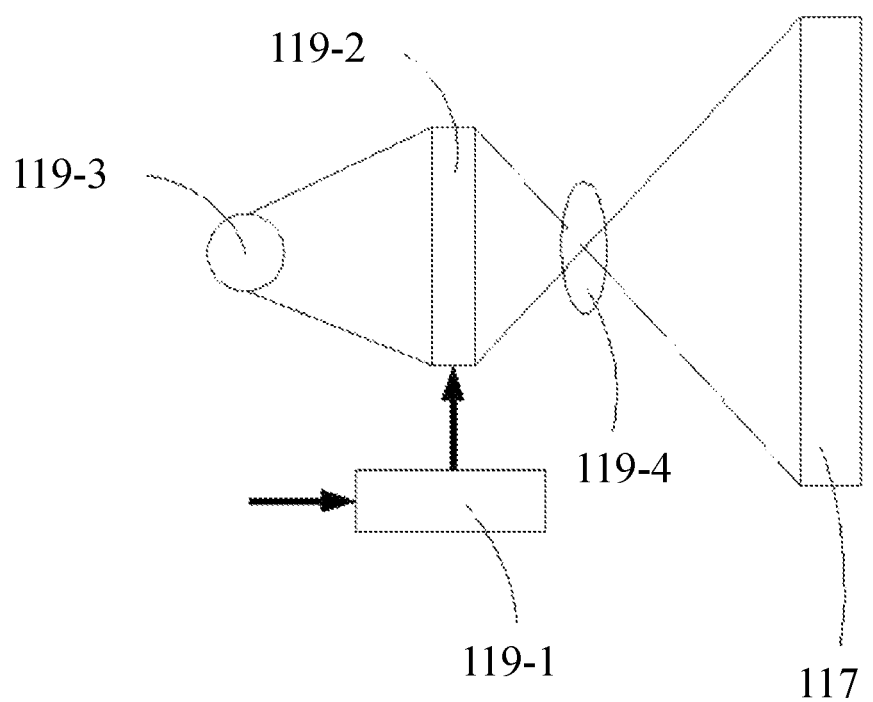
FIG. 8 is a schematic diagram illustrating an exemplary optical projection device according to some embodiments of the present disclosure.

FIG. 8 is a schematic diagram illustrating an exemplary optical projection device 119 in the X-ray imaging device according to some embodiments of the present disclosure. The optical projection device 119 may be configured to project the X-ray image 117 of the subject 118 on the surface of the subject 118.

In some embodiments, the optical projection device may include a driver board 119-1, a display panel 119-2, a light source 119-3, and a lens 119-4 arranged between the display panel 119-2 and the subject 118. The distance between the display panel 119-2 and the lens 119-4 may be adjustable.

Specifically, the driver board 119-1 may be communicatively connected to the X-ray imaging device 110 and the display panel 119-2. The driver board 119-1 may transmit the X-ray image 117 of the subject 118 to the display panel 119-2. In some embodiments, the display panel 119-2 may be a liquid crystal panel without backlight. The light source 119-3 may project the X-ray image displayed on the display panel 119-2 through the lens 119-4 to the surface of the subject 118. In some embodiments, the light source 119-3 may be an LED (Light Emitting Diode) lamp.

It should be noted that the above description of the optical projection device 119 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the optical projection device 119 may include one or more additional components. In some embodiments, one or more components of the optical projection device 119 described above may be omitted.

According to the above description, an exemplary embodiment of systems and methods for controlling the X-ray imaging device 110 is provided. An operator may use the X-ray imaging device 110 to generate an X-ray image 117 of the subject 118. Then the X-ray image 117 may be transmitted to the optical projection device 119 to project on the surface of the subject 118. By visually observing the projected X-ray image 117 on the surface of the subject 118, the operator may determine a desired position to irradiate the X-rays. Then the X-ray source may be adjusted to the desired position to generate a new X-ray image. The new X-ray image may be similarly transmitted to the optical projection device 119 and projected on the surface of the subject 118 again. The operator may further determine whether the newly projected X-ray image is satisfactory (e.g., displaying the region of interest as the operator wants). In this way, the operator may easily obtain the projected X-ray image 117 he/she wants, and may reduce the time of adjusting the X-ray imaging device 110, thus shortening the operation time and reducing the dose of X-rays exposed to the subject.

In some embodiments, the X-ray imaging device 110 may include a mechanical arm configured to achieve surgical operations on the subject. In some embodiments, the mechanical arm may be mechanically connected to a component of the X-ray imaging device 110 (e.g., the C-arm 111).

FIG. 9 is a flowchart illustrating an exemplary process 900 for navigating the mechanical arm according to some embodiments of the present disclosure. In some embodiments, the process 900 may be executed by the X-ray imaging system 100. For example, the process 900 may be implemented as a set of instructions (e.g., an application) stored in one or more storage devices (e.g., the storage device 150, the ROM 230, and/or RAM 240) and invoked and/or executed by the processing device 140 (implemented on, for example, the processor 220 of the computing device 200, the CPU 340 of the mobile device 300, and/or the modules illustrated in FIG. 4). The operations of the process 900 presented below are intended to be illustrative. In some embodiments, the process may be accomplished with one or more additional operations not described, and/or without one or more of the operations discussed. Additionally, the order of the operations of the process 900 as illustrated in FIG. 9 and described below is not intended to be limiting.

In 910, the processing device 140 (e.g., the first coordinate determination module 418) may determine a first coordinate indicating a position of a load in a first coordinate system related to maneuvering of the mechanical arm supporting the load.

For illustration purpose, the X-ray imaging device 110 as illustrated in FIG. 13 is taken as an example. As shown in FIG. 13, the X-ray imaging device 110 may include a gantry 112, a C-arm 111, a lifting column 113, an X-ray source 114-1, a detector 114-2, and a mechanical arm 116. The mechanical arm 116 may be mechanically connected to the C-arm 111. In some embodiments, the mechanical arm 116 may be a multiple-axis mechanical arm. Each axis of the mechanical arm may correspond to an arm segment. In some embodiments, the X-ray imaging device 110 may have two or more mechanical arms similar to or different from the mechanical arm 116.

For illustration purpose, the mechanical arm 116 may be a five-axis mechanical arm. It shall be noted that the mechanical arm 116 may have any other number of axes, which depends on the actual needs and is not limited herein. In some embodiments, a sensor 116-2 may be set at each joint of the mechanical arm 116. Exemplary types of the sensor 116-2 may include a rotation sensor, a displacement sensor, and/or other sensors capable of detecting movement information of the joints of the mechanical arm 116. The movement information of the joints of the mechanical arm 116 may be transmitted to the processing device 140 for calculating the spatial position of the mechanical arm 116 or the load 116-1 mounted on the mechanical arm 116. In some embodiments, the X-ray imaging device 110 may include a pre-processor. The pre-processor may receive the movement information of the mechanical arm 116 and perform a data pre-processing, and then transmit the pre-processed data to the processing device 140.

In some embodiments, the load 116-1 may be fixedly installed at an end of the mechanical arm 116. In some embodiments, depending on actual needs, the load 116-1 may include at least one of an electric drill, a living sampling device, a catheter, a laser light, or the like, or any combination thereof.

In some embodiments, the first coordinate system may be established by the processing device 140 (e.g., the first coordinate determination module 418). The first coordinate system may be related to the maneuvering of the mechanical arm 116. The movement information of the mechanical arm 116 may be represented by the first coordinate system. In some embodiments, any coordinate system that can represent the maneuvering of the mechanical arm 116 may be used as the first coordinate system. For example, the first coordinate system may be a world coordinate system, an inertial coordinate system, a Newtonian coordinate system, or the like, or any combination thereof.

Taking the world coordinate system as an example, the processing device 140 (e.g., the first coordinate determination module 418) may establish a world coordinate system $C_w$, with a coordinate origin $O_w$ and coordinate axes. In some embodiments, the coordinate origin $O_w$ may change with the position of the X-ray imaging device 110. In other words, a movement of the X-ray imaging device 110 may not change a relative positional relationship between the coordinate origin $O_w$ and the X-ray imaging device 110.

Specifically, the processing device 140 (e.g., the first coordinate determination module 418) may determine a central point 115 of the base of the mechanical arm 116 as the coordinate origin $O_w$. When the coordinate origin $O_w$ is set there, a direction in which the lifting column 113 is lifted and lowered may be a Z-axis of the world coordinate system $C_w$, with the vertical upward direction as the positive direction. And a direction in which the X-ray imaging device 110 moves horizontally may be an X-axis, with the direction in which the X-ray imaging device 110 is moving forward as the positive direction. A direction perpendicular to the X-axis and the Z-axis may be a Y-axis. Therefore, the world coordinate system $C_w$ may move with the X-ray imaging device 110, and the coordinate origin $O_w$ may be associated with the position of the X-ray imaging device 110.

Since the load 116-1 of the mechanical arm 116 is fixed on the mechanical arm 116, the first coordinate indicating the position of the load 116 in the world coordinate system $C_w$ may be determined after the world coordinate system $C_w$ is determined. In some embodiments, the first coordinate may be the coordinate of an end point of the load 116-1 away from the mechanical arm 116, the coordinate of a connection point between the load 116-1 and the mechanical arm 116, the coordinate of a specific point of the load 116-1 according to its own characteristics, or the like. For example, assuming that the load is an electric drill, the specific point of the load 116-1 may be the apex of the electric drill.

In some embodiments, the processing device 140 (e.g., the first coordinate determination module 418) may determine one or more mechanical parameters associated with the mechanical arm 116, and then determine the first coordinate indicating the position of the load 116-1 in the first coordinate system based on the one or more mechanical parameters. To determine the one or more mechanical parameters associated with the mechanical arm 116, the processing device 140 (e.g., the first coordinate determination module 418) may determine the position information of at least one joint of the mechanical arm 116 or type information of the load 116-1. Specifically, the processing device 140 (e.g., the first coordinate determination module 418) may acquire a first parameter associated with the rotation of the at least one joint or a second parameter associated with the translation of the at least one joint by the at least one sensor 116-2 periodically, and then determine the position information of the at least one joint of the mechanical arm 116 based on the first parameter associated with the rotation of the at least one joint or the second parameter associated with the translation of the at least one joint. In some embodiments, the type information of the load 116-1 may comprise at least one of an electric drill, a living sampling device, a catheter, or a laser light as described above. More details regarding the determination the first coordinate may be found elsewhere in the present disclosure (e.g., FIG. 11 and FIG. 12, and the relevant descriptions thereof).

In 920, the processing device 140 (e.g., the 3D image obtaining module 420) may obtain a three dimensional (3D) image of the subject, the 3D image representing the subject in a second coordinate system.

In some embodiments, the processing device 140 (e.g., the 3D image obtaining module 420) may obtain a plurality of two dimensional (2D) images based on scan data acquired by the detector at different positions. Optionally, the processing device 140 (e.g., the 3D image obtaining module 420) may correct the plurality of 2D images. And the processing device 140 (e.g., the 3D image obtaining module 420) may reconstruct the 3D image based on the plurality of (corrected) 2D images to obtain a three dimensional (3D) image of the subject 118. For example, the X-ray imaging device 110 may include a pre-processor. The pre-processor may pre-process (e.g., denoise) the 2D images to reconstruct a 3D image, and send the 3D image to the processing device 140 (e.g., the 3D image obtaining module 420). As another example, the processing device 140 (e.g., the 3D image obtaining module 420) may receive the 2D images and process the 2D images (e.g., perform a 3D image reconstruction using a reconstruction algorithm) to reconstruct a 3D image.

In some embodiments, the 3D image may represent the subject in a second coordinate system. For example, the second coordinate system may be an image coordinate system. The coordinate origin of the image coordinate system may be a point that is same as or different from the coordinate origin of the first coordinate system. The coordinate of each voxel (or pixel) of the 3D image in the second coordinate system may correspond to a coordinate of a corresponding physical point of the subject 118 in the first coordinate system. More details regarding obtaining a three dimensional (3D) image of the subject may be found elsewhere in the present disclosure (e.g., FIG. 10 and the relevant descriptions thereof).

In 930, the processing device 140 (e.g., the relationship determination module 422) may determine a relationship between the first coordinate system and the second coordinate system.

In some embodiments, the first coordinate system and the second coordinate system may have different coordinate origins. For example, the first coordinate system may be the world coordinate system $C_w$ with its coordinate origin $O_w$ located at the central point 115 of the base of the mechanical arm 116. And the second coordinate system may be an image coordinate system $C_{3d}$ with the coordinate origin $O_{3d}$ located at a point in the subject 118 (e.g., the iso-center of the X-ray imaging device 110).

In some embodiments, the relationship may be a mapping relationship. The mapping relationship may refer to a relationship between first coordinates of one or more points in the first coordinate system and their corresponding second coordinates in the second coordinate system. Taking a specific point as an example, a mapping relationship $T_{w,3d}$ may indicate a mapping relationship between a first coordinate of the specific point in the world coordinate system and a second coordinate of the specific point in the image coordinate system.

In some embodiments, the mapping relationship between the first coordinate system and the second coordinate system may be in any form such as a table, a matrix, a function, or the like, or any combination thereof. For example, the mapping relationship may be denoted as a table recording the first coordinates of the one or more points in the first coordinate system and their corresponding second coordinates in the second coordinate system. As another example, the mapping relationship may be a transformation matrix determined according to a matrix transformation algorithm. As still another example, the mapping relationship between the world coordinate system and the image coordinate system may be a transformation matrix determined with reference to reconstruction algorithms used for reconstructing the 3D image.

In some embodiments, the first coordinate system may coincide with the second coordinate system. For example, the coordinate origin $O_w$ of the world coordinate system $C_w$ may be set at the center of the subject 118 (e.g., the iso-center of the X-ray imaging device 110), which is also used as a reconstruction center of the 3D image. The center of the subject 118 may be determined by an intersection of beams emitted from at least two different angular positions of the X-ray source 114-1 installed on the arm 111. Specifically, one beam may be parallel to or substantially parallel to the Z-axis direction, and the other beam may be parallel to or substantially parallel to the X-axis direction. Thus the intersection of the two beams may be regarded as the center of the subject 118.

As used herein, if the first coordinate system coincides with the second coordinate system, the two coordinate system may be the same, and the coordinates of a same physical point in the two coordinate systems may be same as each other.

In 940, the processing device 140 (e.g., the coordinate transformation module 424) may transform the first coordinate in the first coordinate system to a second coordinate in the second coordinate system.

In some embodiments, the processing device 140 (e.g., the coordinate transformation module 424) may transform the first coordinate in the first coordinate system to the second coordinate in the second coordinate system based on the relationship between the first coordinate system and the second coordinate system.

For example, the processing device 140 (e.g., the coordinate transformation module 424) may transform the first coordinate in the first coordinate system to a second coordinate in the second coordinate system according to the mapping relationship $T_{w,3d}$ (e.g., a transformation matrix for transforming coordinates between different coordinate systems).

In 950, the processing device 140 (e.g., the displaying module 426) may display a representation of the load in the 3D image at the second coordinate in the second coordinate system.

In some embodiments, the representation of the load 116-1 may be a mark in any form. For example, the mark of the load 116-1 may be, for example, a figure or pattern that is distinctive from the voxels in the 3D image. Exemplary marks may include a pre-stored 3D model that resembles the actual shape of the load, a point with a specific color, or the like.

In some embodiments, taking the image coordinate system $C_{3d}$ and the world coordinate system $C_w$ as an example, if the image coordinate system $C_{3d}$ coincides with the world coordinate system $C_w$, the processing device 140 (e.g., the displaying module 426) may obtain a relative positional relationship between at least one position of the mechanical arm 116 and the center of the subject 118 (i.e., the reconstruction center) in the world coordinate system, and determine the position of the load 116-1 in the image coordinate system $C_{3d}$ based on the relative positional relationship. And the processing device 140 (e.g., the displaying module 426) may further display the representation of the load 116-1 in the 3D image according to the position of the load 116-1 of the mechanical arm 116 in the image coordinate system $C_{3d}$.

It should be noted that the above description of the process 900 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 10:
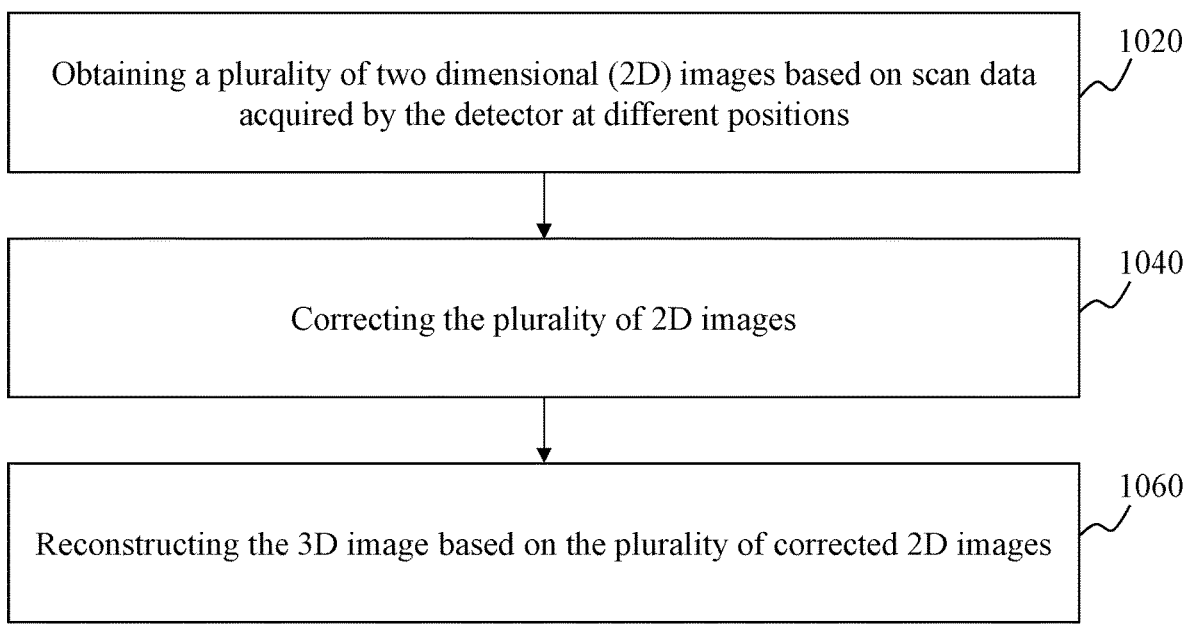
FIG. 10 is a flowchart illustrating an exemplary process for obtaining a 3D image of a subject according to some embodiments of the present disclosure.

FIG. 10 is a flowchart illustrating an exemplary process 1000 for obtaining a 3D image of a subject according to some embodiments of the present disclosure. In some embodiments, the process 1000 may be executed by the X-ray imaging system 100. For example, the process 1000 may be implemented as a set of instructions (e.g., an application) stored in one or more storage devices (e.g., the storage device 150, the ROM 230, and/or RAM 240) and invoked and/or executed by the processing device 140 (implemented on, for example, the processor 220 of the computing device 200, the CPU 340 of the mobile device 300, and/or the modules illustrated in FIG. 4). The operations of the process 1000 presented below are intended to be illustrative. In some embodiments, the process may be accomplished with one or more additional operations not described, and/or without one or more of the operations discussed. Additionally, the order of the operations of the process 1000 as illustrated in FIG. 10 and described below is not intended to be limiting. In some embodiments, one or more operations of the process 1000 may be performed to achieve operation 920.

In 1020, the processing device 140 (e.g., the 3D image obtaining module 420) may obtain a plurality of two dimensional (2D) images based on scan data acquired by the detector at different positions.

In some embodiments, the X-ray imaging device 110 may perform a scan on the subject 118 to acquire scan data. Specifically, the processing device 140 (e.g., the X-ray emitting module 410) may cause the X-ray source 114-1 to emit X-rays to irradiate the subject 118 in different angular directions. The detector 114-2 may be arranged to face the X-ray source 114-1 to detect a portion of the X-rays that pass through the subject 118. The portion of the X-rays that pass through the subject 118 at each angular direction may be used to generate a 2D image. Then the processing device 140 (e.g., the 3D image obtaining module 420) may obtain a plurality of 2D images based on the scan data.

In 1040, the processing device 140 (e.g., the 3D image obtaining module 420) may correct the plurality of 2D images.

In some embodiments, the plurality of 2D images may be distorted due to, for example, the structures of the X-ray imaging device 110 and the imaging algorithm. Exemplary image distortions may include an image distortion caused by mechanical errors, a sigmoid distortion, a pincushion distortion, or the like, or a combination thereof. The processing device 140 (e.g., the 3D image obtaining module 420) may perform image corrections on the plurality of 2D images to reduce the distortion.

For example, exemplary image corrections may include an air correction, a crosstalk correction, an off-focal correction, a beam hardening correction, or the like, or any combination thereof. As another example, the processing device 140 (e.g., the 3D image obtaining module 420) may correct the plurality of 2D images according to one or more correction algorithms and/or correction techniques, such as a beam hardening correction algorithm (e.g., a polynomial fitting algorithm, a Monte Carlo simulation algorithm, an iteration correction algorithm, a dual energy correction algorithm, a single energy correction algorithm), a scattering correction technique (e.g., an image smoothing technique, an image enhancement technique, a Monte Carlo simulation technique, a single scatter simulation (SSS) technique, a dual energy-window technique, a tail fitting technique), or the like, or any combination thereof. In some embodiments, the processing device 140 (e.g., the 3D image obtaining module 420) may perform the image corrections on the 2D images to remove image artifacts, or reduce the noise in the 2D images.

In 1060, the processing device 140 (e.g., the 3D image obtaining module 420) may reconstruct the 3D image based on the plurality of corrected 2D images.

In some embodiments, the processing device 140 (e.g., the 3D image obtaining module 420) may reconstruct the 3D image based on two or more 2D images generated by the X-ray source at different angular directions.

In some embodiments, the processing device 140 (e.g., the 3D image obtaining module 420) may reconstruct the 3D image using a specific reconstruction algorithm, a specific reconstruction technique, a specific reconstruction model, or the like, or any combination thereof. Exemplary reconstruction algorithms may include a shape from texture (SFT) algorithm, a shape from shading (SFS) algorithm, a multi-view stereo (MVS) algorithm, a Moire fringes technique, a time of flight (ToF) technique, a structured light technique, a triangulation technique, or the like, or any combination thereof.

It should be noted that the above description of the process 1000 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 11 is a flowchart illustrating an exemplary process 1100 for determining a first coordinate indicating a position of a load in a first coordinate system according to some embodiments of the present disclosure. In some embodiments, the process 1100 may be executed by the X-ray imaging system 100. For example, the process 1100 may be implemented as a set of instructions (e.g., an application) stored in one or more storage devices (e.g., the storage device 150, the ROM 230, and/or RAM 240) and invoked and/or executed by the processing device 140 (implemented on, for example, the processor 220 of the computing device 200, the CPU 340 of the mobile device 300, and/or the modules illustrated in FIG. 4). The operations of the process 1100 presented below are intended to be illustrative. In some embodiments, the process may be accomplished with one or more additional operations not described, and/or without one or more of the operations discussed. Additionally, the order of the operations of the process 1100 as illustrated in FIG. 11 and described below is not intended to be limiting. In some embodiments, one or more operations of the process 1100 may be performed to achieve operation 910.

In 1120, the processing device 140 (e.g., the first coordinate determination module 418) may determine one or more mechanical parameters associated with the mechanical arm.

In some embodiments, the one or more mechanical parameters associated with the mechanical arm (e.g., the mechanical arm 116) may include the position information of at least one joint of the mechanical arm 116 and/or the type information of the load (e.g., the load 116-1). In some embodiments, the type information of the load may include at least one of an electric drill, a living sampling device, a catheter, or a laser light. It shall be noted that in different application scenarios (e.g., different types of interventional surgeries), the load of the mechanical arm 116 may be different. With different loads, the specific parts (e.g., an apex of the drill) of the loads to be displayed in the 3D image or navigated in the 3D image may be different. In addition, different types of the load of the mechanical arms may have different physical sizes which may also influence the coordinate of the representation of the load in the 3D image.

In some embodiments, the one or more mechanical parameters associated with the mechanical arm may include relative position information between a position of the mechanical arm and the X-ray imaging device 110, one or more physical parameters of the mechanical arm, or the like. For example, the relative position information between a position of the mechanical arm and the X-ray imaging device 110 may include a position of the base of the mechanical arm fixed on the X-ray imaging device 110, and a relative position (e.g., angular position or axial displacement distance, etc.) between adjacent arm segments (e.g., an upper level arm segment and a lower level arm segment) at each joint of the mechanical arm. As another example, the physical parameters of the mechanical arm may include a count of axes of the mechanical arm, sizes of each arm segment of the mechanical arm, or the like.

In some embodiments, the processing device 140 (e.g., the first coordinate determination module 418) may acquire a first parameter associated with a rotation of the at least one joint or a second parameter associated with a translation of the at least one joint, and determine the position information of the at least one joint of the mechanical arm based on the first parameter associated with the rotation of the at least one joint and/or the second parameter associated with the translation of the at least one joint. Details regarding the determination of the position information of the at least one joint of the mechanical arm may be found elsewhere in the present disclosure (e.g., FIG. 12 and the relevant descriptions thereof).

In some embodiments, the one or more mechanical parameters associated with the mechanical arm may be processed by the X-ray imaging system 100 before a diagnosis and/or a treatment (e.g., a surgery). Additionally or alternatively, the one or more mechanical parameters associated with the mechanical arm may also be pre-stored in a storage (e.g., the storage device 150, the ROM 230, or the RAM 240, etc.) according to different types of the mechanical arm.

In 1140, the processing device 140 (e.g., the first coordinate determination module 418) may determine the first coordinate indicating the position of the load in the first coordinate system based on the one or more mechanical parameters.

In some embodiments, the processing device 140 (e.g., the first coordinate determination module 418) may determine the first coordinate indicating the position of the load in the first coordinate system based on the one or more mechanical parameters associated with the mechanical arm and relative position of the mechanical arm with respect to the X-ray imaging device 110 (e.g., the height information of the lifting column of the mechanical arm) by, for example, using a geometric algorithm.

It should be noted that the above description of the process 1100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 12 is a flowchart illustrating an exemplary process 1200 for determining position information of at least one joint of the mechanical arm according to some embodiments of the present disclosure. In some embodiments, the process 1200 may be executed by the X-ray imaging system 100. For example, the process 1200 may be implemented as a set of instructions (e.g., an application) stored in one or more storage devices (e.g., the storage device 150, the ROM 230, and/or RAM 240) and invoked and/or executed by the processing device 140 (implemented on, for example, the processor 220 of the computing device 200, the CPU 340 of the mobile device 300, and/or the modules illustrated in FIG. 4). The operations of the process 1200 presented below are intended to be illustrative. In some embodiments, the process may be accomplished with one or more additional operations not described, and/or without one or more of the operations discussed. Additionally, the order of the operations of the process 1200 as illustrated in FIG. 12 and described below is not intended to be limiting. In some embodiments, one or more operations of the process 1200 may be performed to achieve operation 1120.

In 1220, the processing device 140 (e.g., the first coordinate determination module 418) may acquire a first parameter associated with a rotation of the at least one joint or a second parameter associated with a translation of the at least one joint.

In some embodiments, the processing device 140 (e.g., the first coordinate determination module 418) may acquire the first parameter associated with the rotation of the at least one joint or the second parameter associated with the translation of the at least one joint by at least one sensor periodically.

Specifically, the at least one sensor (e.g., a rotation sensor, a translation sensor) may be installed on the at least one joint of the mechanical arm. The rotation sensor may be used to capture the first parameter associated with the rotation of the at least one joint, and the translation sensor may be used to capture the second parameter associated with the translation of the at least one joint. And the at least one sensor may be communicatively connected to a processor (e.g., the processing device 140) and/or a pre-processor, and may send the first parameter and the second parameter the processor and/or the pre-processor for further processing.

In some embodiments, the operation of acquiring the first parameter associated with the rotation of the at least one joint and/or the second parameter associated with the translation of the at least one joint by the at least one sensor may be performed once every predetermined time interval. For example, the processing device 140 (e.g., the first coordinate determination module 418) may acquire the first parameter and the second parameter automatically according to a preset acquisition frequency. In some embodiments, the acquisition frequency may be not less than a movement frequency of an axis of the mechanical arm and/or a movement frequency of the lifting column of the mechanical arm to avoid inaccuracy of the first parameter and the second parameter.

In 1240, the processing device 140 (e.g., the first coordinate determination module 418) may determine the position information of the at least one joint of the mechanical arm based on the first parameter associated with the rotation of the at least one joint or the second parameter associated with the translation of the at least one joint.

In some embodiments, the processing device 140 (e.g., the first coordinate determination module 418) may update the one or more mechanical parameters associated with the mechanical arm according to the first parameter and the second parameter.

Specifically, after a movement of the mechanical arm, new coordinates of the at least one joint of the mechanical arm in the world coordinate system $C_w$ may be calculated, for example, by a DH parameters (Denavit-Hartenberg parameters) technique. For example, after the processor (e.g., the processing device 140) and/or the pre-processor receives the first parameter and the second parameter, by combining the previous mechanical parameters of the mechanical arm, the processor (e.g., the processing device 140) may obtain a transfer matrix for the at least one joint of the mechanical arm, based on which new coordinates of the at least one joint may be obtained in a mechanical arm coordinate system. The new coordinates of the at least one joint in the mechanical arm coordinate system may be transformed to coordinates in the world coordinate system $C_w$ using a transfer vector $d_A$. The transfer vector $d_A$ may be a displacement vector between the mechanical arm coordinate system and the world coordinate system $C_w$. Then, the position information of the at least one joint (in the world coordinate system $C_w$) may be determined, and may be further sent to the processor (e.g., the processing device 140) to update the corresponding mechanical parameters associated with the mechanical arm.

It should be noted that the above description of the process 1200 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 13 is a schematic diagram illustrating an exemplary X-ray imaging device according to some embodiments of the present disclosure.

One or more casters may be provided at the bottom of the gantry 112 for movement purpose of the X-ray imaging device 110. One end of the lifting column 113 may be connected to the gantry 112, and the other end of the lifting column 113 may be connected to the C-arm 111, so that the movement of the lifting column 113 along the Z-axis may cause the C-arm 111 to translate up and down. The X-ray source 114-1 and the detector 114-2 may be disposed on the C-arm 111. The rotation of the C-arm 111 may cause the X-ray source 114-1 and the detector 114-2 to rotate with the C-arm 111 to reach different angular directions.

In some embodiments, a sensor 116-2 may be set at each joint of the mechanical arm 116. Exemplary sensors may include a rotation sensor, a displacement sensor, and/or other sensors capable of detecting the movement information of the joints of the mechanical arm 116. The movement information of the mechanical arm 116 may be transmitted to the processing device 140 for calculating the spatial position of the mechanical arm 116 or the load 116-1 mounted on the mechanical arm 116.

In some embodiments, the load 116-1 may be fixedly installed at an end of the mechanical arm 116. In some embodiments, depending on actual needs, the load 116-1 may include an electric drill, a living sampling device, a catheter, a laser light, or the like, or any combination thereof.

It should be noted that the above description of the X-ray imaging device 110 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the X-ray imaging device 110 may include one or more additional components. In some embodiments, one or more components of the X-ray imaging device 110 described above may be omitted.

According to the above description, an exemplary embodiment of systems and methods for navigating the mechanical arm 116 is provided. According to the operations in the embodiments, it is possible to implement navigation for the mechanical arm 116. In this way, navigation accuracy and surgery safety may be improved. At the same time, since the first coordinate system associated with the position of the X-ray imaging device 110 is established and changes with the X-ray imaging device 110, even if the X-ray imaging device 110 moves, there may be no need to re-register the first coordinate system, which may greatly simplify navigation process of the mechanical arm 116. In addition, the display of the load in the 3D image may better present the spatial relationship between the load and the patient, which facilitates execution of the surgery, greatly reduces the complexity of the operation during the surgery.

Figure 14:
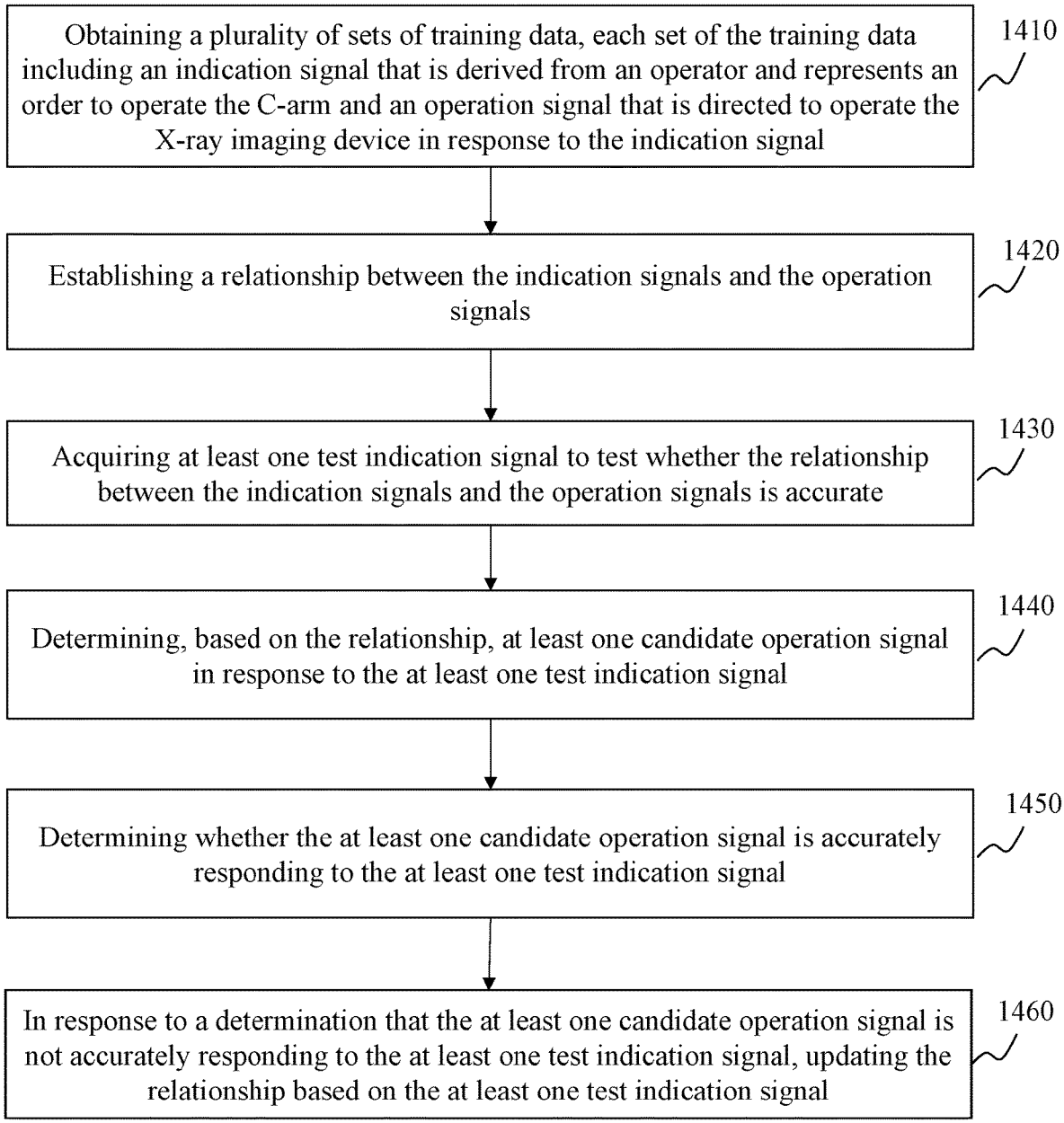
FIG. 14 is a flowchart illustrating an exemplary process for training the X-ray imaging device according to some embodiments of the present disclosure.

FIG. 14 is a flowchart illustrating an exemplary process 1400 for training the X-ray imaging device according to some embodiments of the present disclosure. In some embodiments, the process 1400 may be executed by the X-ray imaging system 100. For example, the process 1400 may be implemented as a set of instructions (e.g., an application) stored in one or more storage devices (e.g., the storage device 150, the ROM 230, and/or RAM 240) and invoked and/or executed by the processing device 140 (implemented on, for example, the processor 220 of the computing device 200, the CPU 340 of the mobile device 300, and/or the modules illustrated in FIG. 4). The operations of the process 1400 presented below are intended to be illustrative. In some embodiments, the process may be accomplished with one or more additional operations not described, and/or without one or more of the operations discussed. Additionally, the order in which the operations of the process 1400 as illustrated in FIG. 14 and described below is not intended to be limiting.

In 1410, the processing device 140 (e.g., the training data obtaining module 428) may obtain a plurality of sets of training data. Each set of the training data may include an indication signal and an operation signal.

In some embodiments, the indication signal may be derived from an operator (e.g., a doctor, a technician) and represent an order to operate the X-ray imaging device 110. The indication signal may include at least one of a voice command or an image command. As used herein, the voice command may be a command given to the X-ray imaging device 110 through the voice of the operator. The image command may be a command given to the X-ray imaging device through one or more images of the operator. For example, the processing device 140 may analyze one or more images representing the operator's gesture action to generate a command of the operator.

In some embodiments, the operation signal may be directed to operate the X-ray imaging device 110 in response to the indication signal. In some embodiments, the operation signal may indicate the action to be performed by the X-ray imaging device 110. Exemplary operation signals may include a position adjustment of the X-ray imaging device 110 of the X-ray imaging device 110, a parameter setting, or a starting of X-ray imaging of the X-ray imaging device 110, or the like, or a combination thereof.

In some embodiments, the indication signal may be collected by an acquisition device such as a visible light sensor (e.g., a camera), and/or an audio sensor (e.g., a microphone). The acquisition device may be installed on the X-ray imaging device 110 or other device near the X-ray imaging device 110 to monitor a region where the operator appears.

Specifically, in one set of the training data, the indication signal may be derived from a doctor, and the operation signal may be input by a technician who understands the meaning of the indication signal and directly operates the X-ray imaging device 110 to perform operations corresponding to the indication signal. In some embodiments, the corresponding operations may control, for example, a movement of the X-ray imaging device 110, a rotation of the C-arm of the X-ray imaging device, or the like. In some embodiments, the corresponding operations may be various parameter settings for X-ray imaging, such as a voltage (kV), a current (mA), a time (ms), a frame rate of images, or other optimized settings for images, or the like. Additionally or alternatively, the corresponding operations may be a starting and/or an ending of X-ray imaging. In some embodiments, the operation signal may be collected by a signal input device such as a touch screen, a keyboard, various types of switch buttons, a hand brake, a foot brake, or the like.

In 1420, the processing device 140 (e.g., the relationship establishing module 430) may establish a relationship between the indication signals and the operation signals.

In some embodiments, the relationship between the indication signals and the operation signals may be represented by a relational database or a specific model.

After a sufficient number of indication signals (e.g., indications signals from a doctor) and corresponding operation signals (e.g., operation signals from a technician) are collected, a plurality of sets of indication signals and operation signals may be used to establish the relational database. In some embodiments, the relationships between the indication signals and the operation signals may be established using a machine learning process including a neural network. In the relationship, one or more indication signals may correspond to one operation signal. For example, a voice command and a gesture action (i.e., an image command) may correspond to a same operation signal, or two or more voice commands expressed in different manners may correspond to a same operation signal. Under this circumstance, the operator (e.g., the doctor) giving the indication signal may initiate a command according to his/her own habit, which is flexible and convenient.

In some embodiments, the processing device 140 (e.g., the relationship establishing module 430) may establish the relationship between the indication signals and the operation signals using a specific model. Specifically, the processing device 140 (e.g., the relationship establishing module 430) may collect and/or record indication signals of the first operator (e.g. a doctor) and corresponding operation signals of the second operator (e.g., a technician), for example, in a preset time period (e.g., in the last week, in the last month, in the last year, etc.). And the processing device 140 (e.g., the relationship establishing module 430) may train the specific model using the collected and/or recorded signals. In the training process, the indication signals may be used as inputs of the specific model and the operation signals may be used as the corresponding outputs. After specific model is trained with sufficient training data, the processing device 140 (e.g., the relationship establishing module 430) may obtain an operation signal as the output of the trained model when using an indication signal as the input of the trained model.

In 1430, the processing device 140 (e.g., the test indication signal acquiring module 432) may acquire at least one test indication signal to test whether the relationship between the indication signals and the operation signals is accurate.

In some embodiments, the processing device 140 (e.g., the test indication signal acquiring module 432) may acquire the at least one test indication signal from an operator (e.g. a doctor). For example, the processing device 140 (e.g., the test indication signal acquiring module 432) may acquire the at least one test indication signal using an acquisition device such as a visible light sensor (e.g., a camera), or an audio sensor (e.g., a microphone).

In some embodiments, the processing device 140 (e.g., the test indication signal acquiring module 432) may acquire the at least one test indication signal using a simulated technique. For example, the processing device 140 (e.g., the test indication signal acquiring module 432) may simulate one or more indication signals in the training data to generate the at least one test indication signal.

In 1440, the processing device 140 (e.g., the candidate operation signal determination module 434) may determine, based on the relationship, at least one candidate operation signal in response to the at least one test indication signal.

In some embodiments, the processing device 140 (e.g., the candidate operation signal determination module 434) may determine the at least one candidate operation signal in response to the at least one test indication signal based on the relational database. For example, after receiving a gesture action or a voice command of a first operator through a visible light sensor or an audio sensor, the processing device 140 (e.g., the candidate operation signal determination module 434) may generate an operation signal matching the indication signal based on the established relationship between the indication signals and the operation signals (e.g., the relational database), and then direct the X-ray imaging device 110 to perform the corresponding operations automatically.

In some embodiments, the processing device 140 (e.g., the candidate operation signal determination module 434) may determine the at least one candidate operation signal in response to the at least one test indication signal based on the trained model.

For example, the processing device 140 (e.g., the candidate operation signal determination module 434) may receive the at least one test indication signal as the input of the trained model, and then obtain the at least one candidate operation signal as the output of the trained model.

In 1450, the processing device 140 (e.g., the determination module 436) may determine whether the at least one candidate operation signal is accurately responding to the at least one test indication signal.

In some embodiments, a second operator may evaluate whether the at least one candidate operation signal is accurately responding to the at least one test indication signal through the processing device 140 (e.g., the determination module 436). For example, the at least one candidate operation signal may be displayed on a screen in a form of a text or a pattern, and the second operator may input a determination on whether the at least one candidate operation signal accurately matches the test indication signal.

In some embodiments, the at least one test indication signal may include a plurality of test indication signals, and the processing device 140 (e.g., the determination module 436) may determine whether the at least one candidate operation signal is accurately responding to the at least one test indication signal by determining a matching rate between the plurality of test indication signals and the corresponding candidate operation signals.

The matching rate may indicate an accuracy of the processing device 140 for predicting candidate operation signals according to the test indication signals and the established relationship between the indication signals and the operation signals.

In some embodiments, the determination that the at least one candidate operation signal is not accurately responding to the at least one test indication signal may include that the matching rate between the plurality of test indication signals and the corresponding candidate operation signals is lower than a preset value.

For example, the preset value may be set as 90%, 95%, or any other suitable value. If the matching rate is lower than the preset value, the processing device 140 (e.g., the determination module 436) may determine that the at least one candidate operation signal is not accurately responding to the at least one test indication signal. As such, the established relationship between the indication signals and the operation signals may be regarded as inaccurate, and the X-ray imaging device 110 may not be deemed to accurately generate a correct operation according to an indication signal. Thus, the X-ray imaging device 110 may not be able to work without the supervision of an operator, and the established relationship between the indication signals and the operation signals may be updated to further improve the accuracy.

In 1460, the processing device 140 (e.g., the relationship update module 438) may, in response to a determination that the at least one candidate operation signal is not accurately responding to the at least one test indication signal, update the relationship based on the at least one test indication signal.

In some embodiments, the relational database may be updated to include the at least one test indication signal and its corresponding operation signal(s). In some embodiments, the relational database may be updated to modify existing relations between the indication signals and an operation signals if there is an error or conflict. In some embodiments, if a missing corresponding relation is found, for example, a specific indication signal (e.g., the indication signal of a specific operator) have no corresponding operation signal, or the indication signals of a specific operator have not been recorded, the missing corresponding relation may be added into the relational database.

Specifically, the X-ray imaging device 110 may work in a semi-automatic state with the assistance of a second operator (e.g., a technician) to update the established relationship. For example, after a first operator (e.g., a doctor) sends an indication signal, the processing device 140 (e.g., the candidate operation signal determination module 434) may determine a candidate operation signal based on the relationship and send (e.g., by the determination module 436) the candidate operation signal to the second operator to determine whether the candidate operation signal matches the indication signal of the first operator. If the candidate operation signal matches the indication signal of the first operator, the second operator may confirm that the X-ray imaging device 110 may perform the corresponding operation according to the candidate operation signal. If the candidate operation signal does not match the indication signal of the first operator, the second operator may modify the candidate operation signal. The processing device 140 (e.g., the relationship update module 438) may record the modified candidate operation signal to update the relationship between the indication signals and the operation signals.

It should be noted that the above description of the process 1400 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the determination that the at least one candidate operation signal is not accurately responding to the at least one test indication signal may include or not include that the matching rate between the plurality of test indication signals and the corresponding candidate operation signals is equal to than a preset value.

Figure 15:
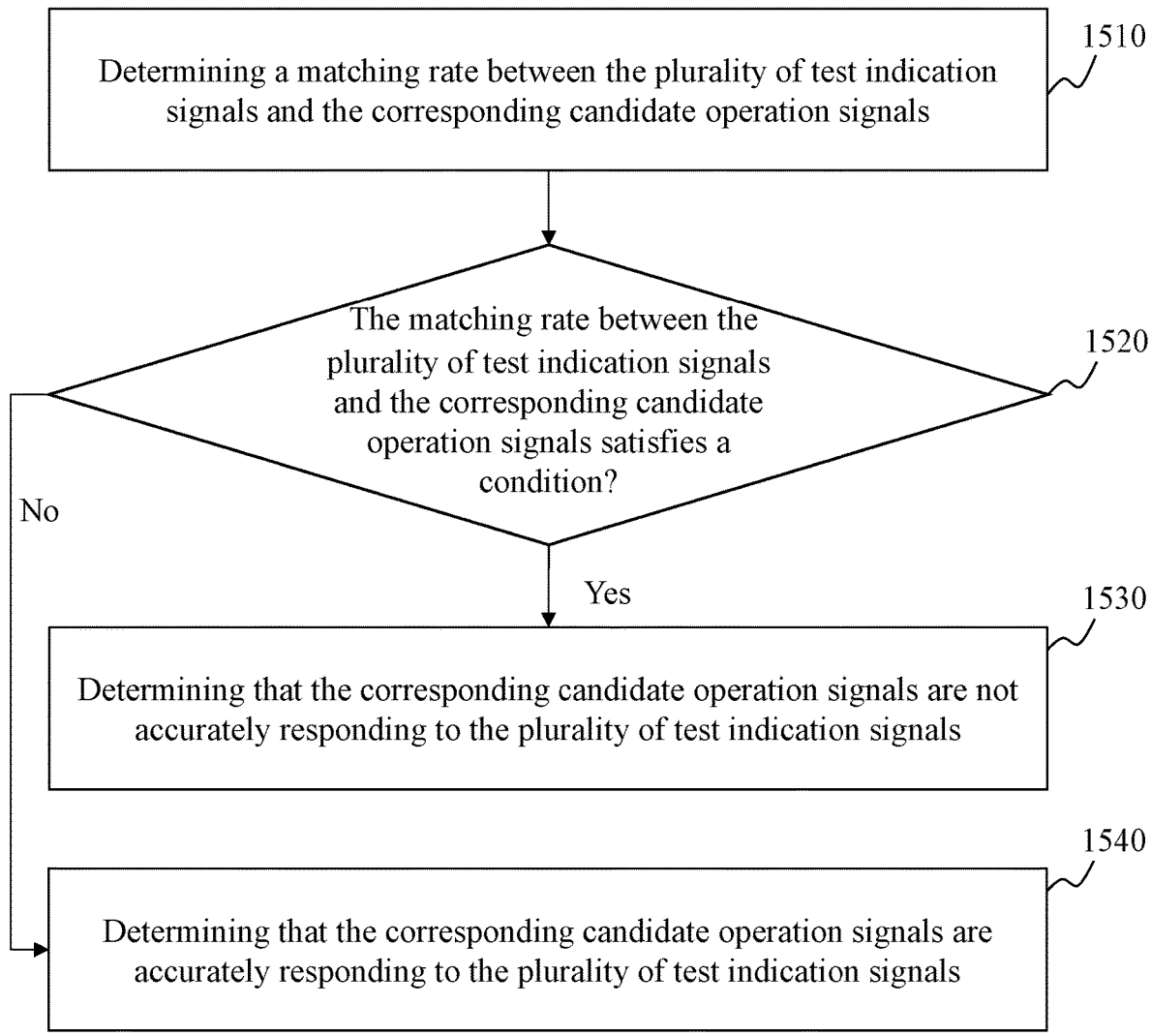
FIG. 15 is a flowchart illustrating an exemplary process for determining whether at least one candidate operation signal is accurately responding to at least one test indication signal according to some embodiments of the present disclosure.

FIG. 15 is a flowchart illustrating an exemplary process 1500 for determining whether at least one candidate operation signal is accurately responding to at least one test indication signal according to some embodiments of the present disclosure. In some embodiments, the process 1500 may be executed by the X-ray imaging system 100. For example, the process 1500 may be implemented as a set of instructions (e.g., an application) stored in one or more storage devices (e.g., the storage device 150, the ROM 230, and/or RAM 240) and invoked and/or executed by the processing device 140 (implemented on, for example, the processor 220 of the computing device 200, the CPU 340 of the mobile device 300, and/or the modules illustrated in FIG. 4). The operations of the process 1500 presented below are intended to be illustrative. In some embodiments, the process may be accomplished with one or more additional operations not described, and/or without one or more of the operations discussed. Additionally, the order of the operations of the process 1500 as illustrated in FIG. 15 and described below is not intended to be limiting. In some embodiments, one or more operations of the process 1500 may be performed to achieve operation 1450.

In 1510, the processing device 140 (e.g., the determination module 436) may determine a matching rate between the plurality of test indication signals and the corresponding candidate operation signals.

In some embodiments, the processing device 140 (e.g., the determination module 436) may calculate the matching rate using an algorithm, a function, a model, or the like. For example, the processing device 140 (e.g., the determination module 436) may calculate the matching rate by dividing the count of candidate operation signals that matches the test indication signals by the count of all the candidate operation signals. The matching rate may be in the form of a percentage, a fraction, or the like, or any combination thereof.

In 1520, the processing device 140 (e.g., the determination module 436) may determine whether the matching rate between the plurality of test indication signals and the corresponding candidate operation signals satisfies a condition.

In some embodiments, the processing device 140 (e.g., the determination module 436) may determine a preset value for the matching rate, and the condition may be that the matching rate is lower than the preset value. For example, the preset value may be set as 90%, 95%, or any other suitable value. The processing device 140 (e.g., the determination module 436) may compare the matching rate and the preset value to determine whether the matching rate between the plurality of test indication signals and the corresponding candidate operation signals is lower than the preset value. If the matching rate between the plurality of test indication signals and the corresponding candidate operation signals is lower than the preset value, the process 1500 may proceed to operation 1530. If the matching rate between the plurality of test indication signals and the corresponding candidate operation signals is not lower than the preset value, the process 1500 may proceed to operation 1540.

In 1530, the processing device 140 (e.g., the determination module 436) may determine that the corresponding candidate operation signals are not accurately responding to the plurality of test indication signals.

In 1540, the processing device 140 (e.g., the determination module 436) may determine that the corresponding candidate operation signals are accurately responding to the plurality of test indication signals.

It should be noted that the above description of the process 900 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the condition may include or not include that the matching rate between the plurality of test indication signals and the corresponding candidate operation signals is equal to than a preset value.

According to the above description, an exemplary embodiment of systems and methods for training the X-ray imaging device 110 is provided. Based on the systems and methods, a relationship of indication signals of a doctor and operations signals of the X-ray imaging device 110 may be established. In an application scenario, after receiving indication signals of the operator (e.g., a gesture action or a voice command) through a visible light sensor or an audio sensor, the X-ray imaging device 110 may generate an operation signal correspondingly and may operate automatically. As such, the X-ray imaging device 110 may work under no supervision of a technician, which may save human resources and reduce operational errors caused by technicians. In another aspect, the doctor may directly send instructions to the X-ray imaging device 110 according to his/her own habits to improve the efficiency of diagnoses and treatments.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method, implemented on a computing device having one or more processors and one or more storage media, the method comprising:
   causing an X-ray source to emit X-rays to irradiate a subject;
   generating an X-ray image of the subject, wherein the X-ray image is generated using a detector that is arranged to face the X-ray source to detect a portion of the X-rays that pass through the subject;
   causing to project, using an optical projection device, the X-ray image of the subject on a surface of the subject;
   determining one or more adjustment parameters based on the projected X-ray image;
   adjusting, based on the one or more adjustment parameters, a position of at least one of the X-ray source or the detector relative to the subject to obtain a second X-ray image; and
   causing to project, using the optical projection device, the second X-ray image on the surface of the subject, wherein the second X-ray image includes one or more regions of the subject that are different from one or more regions of the subject included in the X-ray image.

2. The method of claim 1, wherein the causing to project, using an optical projection device, the X-ray image of the subject on a surface of the subject comprises:
   causing to project at least part of the X-ray image on the surface of the subject at a region where the X-rays irradiate the subject.

3. The method of claim 1, wherein
   the X-ray source and the detector are installed at two ends of a C-arm of an X-ray imaging device, respectively; and
   the one or more adjustment parameters include a direction or an angle of a rotation of the C-arm.

4. The method of claim 1, wherein the optical projection device comprises a driver board, a display panel, and a light source, wherein the causing to project, using the optical projection device, the X-ray image of the subject on the surface of the subject comprises:
   causing, using the driver board, the display panel to display the X-ray image; and
   causing to emit, using the light source, a light towards the display panel to project the displayed X-ray image on the surface of the subject.

5. The method of claim 1, comprising:
   causing to receive, by a workstation, the X-ray image of the subject; and
   transmitting the X-ray image to the optical projection device.

6. The method of claim 1, wherein the determining one or more adjustment parameters based on the projected X-ray image comprises:
   determining the one or more adjustment parameters based on the projected X-ray image using a learning module, wherein the learning module is trained with historical projected X-ray images and one or more adjustment parameters associated with corresponding subsequent manual operations of an operator.

7. The method of claim 3, comprising:
   causing to generate, using an optical positioning device, a position mark within the projected X-ray image on the surface of the subject.

8. The method of claim 3, further comprising navigating a mechanical arm, the mechanical arm supporting a load and being mechanically connected to the C-arm, the method comprising:
   determining a first coordinate indicating a position of the load in a first coordinate system related to maneuvering of the mechanical arm;

obtaining a three dimensional (3D) image of the subject, the 3D image representing the subject in a second coordinate system;

determining a relationship between the first coordinate system and the second coordinate system;

transforming the first coordinate in the first coordinate system to a second coordinate in the second coordinate system; and displaying a representation of the load in the 3D image at the second coordinate in the second coordinate system.

9. A method of claim 3, further comprising:

obtaining a plurality of sets of training data, each set of the training data including an indication signal that is derived from an operator and represents an order to operate the C-arm and an operation signal that is directed to operate the C-arm in response to the indication signal;

establishing a relationship between the indication signals and the operation signals;

acquiring at least one test indication signal;

determining, based on the relationship, at least one candidate operation signal in response to the at least one test indication signal;

determining whether the at least one candidate operation signal is accurately responding to the at least one test indication signal; and in response to a determination that the at least one candidate operation signal is not accurately responding to the at least one test indication signal, updating the relationship based on the at least one test indication signal.

10. The method of claim 4, wherein the optical projection device includes a lens arranged between the display panel and the subject, and a distance between the display panel and the lens is adjustable.

11. The method of claim 8, wherein the first coordinate system and the second coordinate system are associated with different coordinate origins, wherein the determining a relationship between the first coordinate system and the second coordinate system comprises:

calculating a mapping relationship between the first coordinate system and the second coordinate system.

12. The method of claim 8, wherein the obtaining a 3D image of the subject comprises:

obtaining a plurality of two dimensional (2D) images based on scan data acquired by the detector at different positions; and reconstructing the 3D image based on the plurality of 2D images.

13. The method of claim 8, wherein the determining a first coordinate indicating a position of the load in a first coordinate system comprises:

determining one or more mechanical parameters associated with the mechanical arm; and determining the first coordinate indicating the position of the load in the first coordinate system based on the one or more mechanical parameters.

14. The method of claim 12, wherein the reconstructing the 3D image based on the plurality of 2D images comprises:

correcting the plurality of 2D images; and reconstructing the 3D image based on the plurality of corrected 2D images.

15. The method of claim 13, wherein the determining one or more mechanical parameters associated with the mechanical arm comprises:

determining position information of at least one joint of the mechanical arm or type information of the load.

16. The method of claim 15, wherein the determining position information of at least one joint of the mechanical arm comprises:

acquiring a first parameter associated with a rotation of the at least one joint or a second parameter associated with a translation of the at least one joint; and determining the position information of the at least one joint of the mechanical arm based on the first parameter associated with the rotation of the at least one joint or the second parameter associated with the translation of the at least one joint.

17. The method of claim 16, wherein the acquiring a first parameter associated with a rotation of the at least one joint or a second parameter associated with a translation of the at least one joint comprises:

acquiring the first parameter associated with the rotation of the at least one joint or the second parameter associated with the translation of the at least one joint by at least one sensor periodically.

18. The method of claim 9, wherein the at least one test indication signal includes a plurality of test indication signals, and the determining whether the at least one candidate operation signal is accurately responding to the at least one test indication signal comprises:

determining a matching rate between the plurality of test indication signals and the corresponding candidate operation signals.

19. The method of claim 9, wherein the indication signals include at least one of a voice command or an image command, and the operation signals include at least one of a position adjustment, a parameter setting, or a starting of X-ray imaging with the X-ray imaging device.

20. The method of claim 18, wherein the determination that the at least one candidate operation signal is not accurately responding to the at least one test indication signal includes that the matching rate between the plurality of test indication signals and the corresponding candidate operation signals is lower than a preset value.

* * * * *